(12) United States Patent
Johnson et al.

(10) Patent No.: US 10,905,330 B2
(45) Date of Patent: Feb. 2, 2021

(54) MODULAR PATIENT AND ANTENNA SUPPORT STRUCTURE FOR MAGNETIC RESONANCE IMAGING

(71) Applicant: Neocoil, LLC, Pewaukee, WI (US)

(72) Inventors: Kyle Johnson, Brookfield, WI (US); Brian Brown, Wauwatosa, WI (US); Chris Salimes, Brookfield, WI (US); Emad Abdelsalam, Milwaukee, WI (US)

(73) Assignee: NeoCoil, Inc., Pewaukee, WI (US)

( * ) Notice: Subject to any disclaimer, the term of this patent is extended or adjusted under 35 U.S.C. 154(b) by 928 days.

(21) Appl. No.: 14/952,701

(22) Filed: Nov. 25, 2015

(65) Prior Publication Data

US 2017/0143204 A1    May 25, 2017

(51) Int. Cl.
*A61B 5/00* (2006.01)
*G01R 33/34* (2006.01)
*A61B 5/055* (2006.01)

(52) U.S. Cl.
CPC ............ *A61B 5/004* (2013.01); *A61B 5/0555* (2013.01); *A61B 5/708* (2013.01); *G01R 33/34* (2013.01)

(58) Field of Classification Search
None
See application file for complete search history.

(56) References Cited

U.S. PATENT DOCUMENTS

| | | | | |
|---|---|---|---|---|
| 5,808,468 A | * | 9/1998 | Bis | A61B 5/0555 324/318 |
| 2005/0228267 A1 | * | 10/2005 | Bulkes | A61B 6/0414 600/415 |
| 2007/0016003 A1 | * | 1/2007 | Piron | A61B 5/415 600/415 |
| 2008/0129293 A1 | * | 6/2008 | Schnell | A61B 5/0555 324/318 |
| 2009/0027053 A1 | * | 1/2009 | Decke | A61B 5/0555 324/318 |
| 2014/0024926 A1 | | 1/2014 | Piron et al. | |
| 2014/0121499 A1 | * | 5/2014 | Coppens | A61B 5/0555 600/422 |
| 2014/0213886 A1 | * | 7/2014 | Menon | A61B 10/0275 600/411 |
| 2016/0022142 A1 | * | 1/2016 | Bradshaw | A61B 5/0555 600/415 |
| 2017/0143203 A1 | * | 5/2017 | Yang | A61B 5/004 |

* cited by examiner

*Primary Examiner* — Katherine L Fernandez
(74) *Attorney, Agent, or Firm* — Boyle Fredrickson, SC

(57) ABSTRACT

The subject matter disclosed herein describes an improved MR imaging system for breast tissue. The MR imaging system includes a pair of antenna coil arrays that are movable with respect to a base plate on which the coil arrays are mounted. A fixed coil array may also be mounted in a medial location on the base plate. The MR imaging system provides an abdominal support structure and a head support structure to position a patient in a prone position over the movable and fixed coil arrays. An additional support pad may be provided on the upper surface of the medial coil to support the patient's chest. Each of the movable antenna coil arrays may be moved laterally along the base plate to adjust the space between the two arrays. Once adjusted, each of the movable antenna coil arrays may be secured in the adjusted position to immobilize the breast tissue.

15 Claims, 33 Drawing Sheets

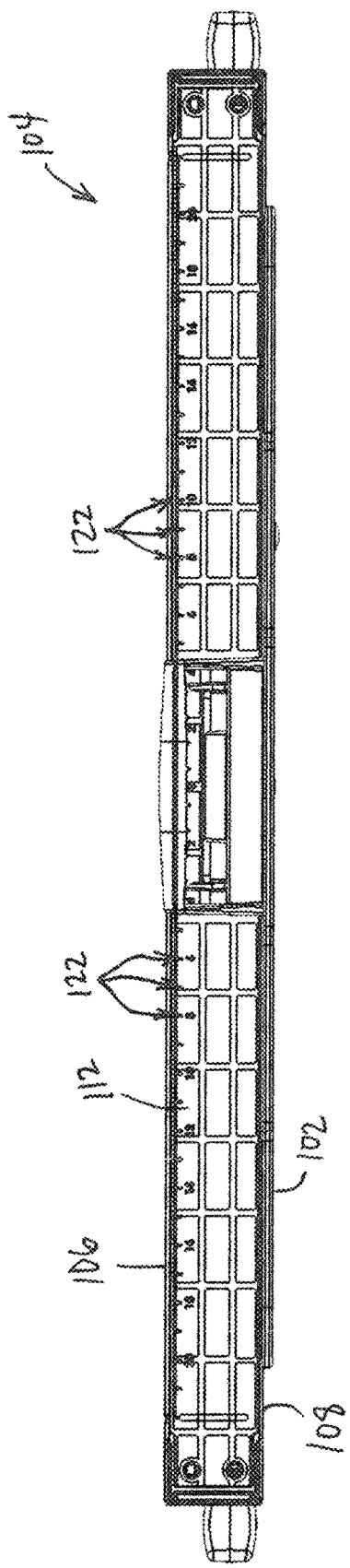
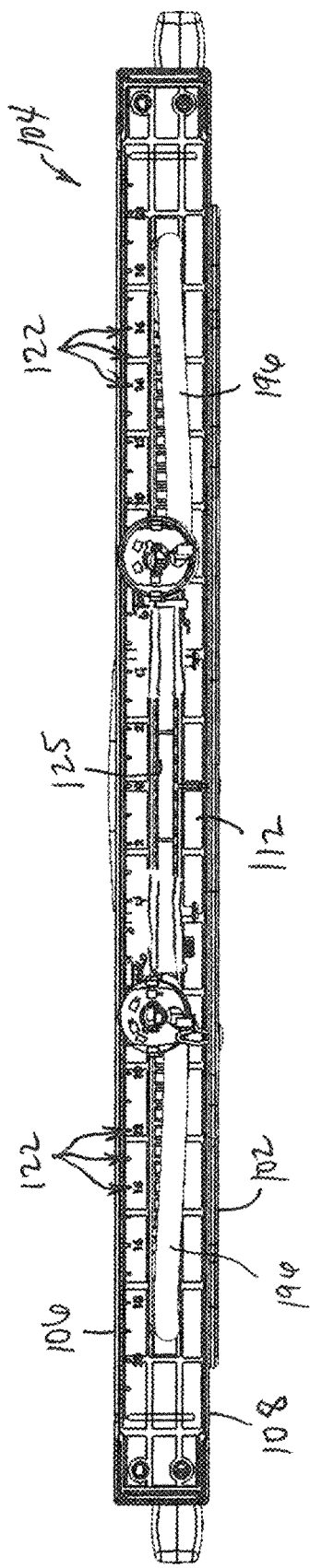
FIG. 35
FIG. 36

MODULAR PATIENT AND ANTENNA SUPPORT STRUCTURE FOR MAGNETIC RESONANCE IMAGING

BACKGROUND OF THE INVENTION

The subject matter disclosed herein relates to a system for use in obtaining a magnetic resonance (MR) image of the breast tissue of a patient. More specifically, the assembly includes support structures both for patient comfort and stability as well as structures to position both the antenna arrays and the breast tissue of the patient when obtaining the (MR) image.

As is known to those skilled in the art, an MR system alternately generates a strong magnetic field and then detects the faint nuclear magnetic resonance (NMR) signals given off by nuclei in the presence of the magnetic field. The NMR signals vary as a function of the type of organ, bone, tissue, etc. . . . present within the magnetic field. The NMR signals are received by antennas, also known as coils, and transmitted to the MR scanner for reconstruction into an MR image. Specifically, an anatomical region of a patient is located within the magnetic field and proximate to the antennas. The MR scanner reconstructs the NMR signals into an MR image corresponding to the anatomical region of the patient being imaged.

As is also known to those skilled in the art, obtaining an MR image of breast tissue presents several challenges, and the quality of the MR image obtained may be impacted by a number of factors. If for example, the anatomical region being imaged moves, or is moved, during the scan, a motion artifact may be introduced. Even if a patient is not intentionally moving, respiration of a patient can cause the chest and, therefore, the breast tissue to move. Thus, it would be desirable to provide an imaging system that immobilizes the breast tissue prior to executing an MR scan.

In addition, the signal-to-noise ratio (SNR) of an MR image decreases, reducing the overall quality, as the distance from the anatomical region to be imaged and the antenna detecting the NMR signals increases. It is known that a surface coil provides improved SNR because the coil is placed against the anatomical region to be imaged. However, breast tissue can vary significantly in size between patients and, therefore, it is difficult to provide a single surface coil that works effectively for multiple patients. Thus, it would be desirable to provide an imaging system that is adjustable to accommodate the varying size of breast tissue.

Further, some procedures require imaging of a single breast while other procedures require imaging of both breasts. Thus, it would be desirable to provide an imaging system configurable to obtain an MR image of either a single breast or of both breasts of a patient.

BRIEF DESCRIPTION OF THE INVENTION

The subject matter disclosed herein describes an improved MR imaging system for breast tissue. The MR imaging system includes a pair of antenna coil arrays that are movable with respect to a base plate on which the coil arrays are mounted. A fixed coil array may also be mounted in a central, or medial, location on the base plate. The MR imaging system is configured to position a patient in a prone position over the movable and fixed coil arrays such that the breast tissue is suspended between one of the movable coil arrays and the fixed coil array. A first patient support structure is movable on the scan table such that it is located generally below a patient's abdomen. A second patient support structure is also movable on the scan table such that it is located below a patient's face. The patient lays on the first patient support structure, over the coil arrays, and rests the forehead and sides of the face on pads on the second support structure. An additional support pad may be provided on the upper surface of the medial coil array such the patient's chest may rest on the medial coil array. Each of the movable antenna coil arrays may be moved laterally along the base plate toward and away from the medial coil array to adjust the space and to accommodate varying sized breast tissue between the two arrays. Once adjusted, each of the movable antenna coil arrays may be secured in the adjusted position to immobilize the breast tissue prior to executing an MR scan. Finally, each of the antenna arrays is removably mounted to the base plate. Thus, either a combination of the medial coil and one movable coil or two movable coils may be mounted to the base plate and positioned to provide for imaging of a single breast. Using both movable coils and the medial coil, both breasts may be imaged in tandem.

In one embodiment of the invention, a modular patient and antenna support system movable with respect to a surface on which it is located during medical imaging is disclosed. The modular patient and antenna support system includes a first and second patient support structure and an antenna support structure. The first patient support structure is movable to engage a first anatomy of a patient and to, at least in part, support the patient. The second patient support structure is movable to engage a second anatomy of the patient and to, at least in part, support the patient. The first and second patient support structures are movable independent of each other. The antenna support structure is movably positioned between the first patient support structure and the second patient support structure, and the antenna support structure is movable to receive an anatomy of the patient to be imaged. The antenna support structure includes a plurality of antenna arrays and a base plate operable to receive the plurality of antenna arrays. A first antenna array, selected from the plurality of antenna arrays, is movable with, respect to the base plate when mounted to the base plate.

According to another aspect of the invention, each of the plurality of antenna arrays may be removably mounted to the base plate. A second antenna array, selected from the plurality of antenna arrays, may be fixed with respect to the base plate when mounted to the base plate. The first antenna array is moved along the base plate to position the anatomy of the patient to be imaged between the first antenna array and the second antenna array.

It is contemplated that the anatomy of the patient to be imaged is a first breast and a second breast. A third antenna array, selected from the plurality of antenna arrays, may be included and be movable with respect to the base plate when mounted to the base plate, and the first and third antenna arrays are positioned on opposite sides of the second antenna array. The first antenna array may be moved along the base plate to position the first breast between the first antenna array and the second antenna array, and the third antenna array is moved along the base plate to position the second breast between the third antenna array and the second antenna array such that the first and second breasts may be imaged in tandem.

It is further contemplated that the anatomy of the patient to be imaged is one breast of the patient. The second antenna array may be mounted to the base plate, as indicated above. Optionally, the second antenna array may be movable with respect to the base plate when mounted to the base plate, and the first and second antenna arrays are moved along the base plate to position the breast of the patient for imaging between the first antenna array and the second antenna array.

According to still another aspect of the invention, one of the first and the second antenna arrays may include a biopsy grid. The second antenna array, when mounted to the base plate, may include a support surface distal from the base plate. The support surface engages a third anatomy of the patient to, at least in part, support the patient. At least one rail may be mounted to the base plate, and a carriage may be movably connected to the at least one rail. An antenna array movable with respect to the base plate may be removably mounted to the carriage where the carriage moves the antenna array with respect to the base plate.

According to another embodiment of the invention, a connection system for use between an antenna array and a scanner during medical imaging is disclosed. The connection system includes a housing within which the antenna array is mounted. The housing includes a mating surface with an opening extending therethrough. A first electrical connector is in communication with the antenna array and is mounted, at least in part within the housing. The first electrical connector is accessible via the opening in the mating surface. A carriage is movably mounted to a base plate, where the carriage includes a mating surface complementary to the mating surface of the housing. The housing is removably mounted to the carriage, and the mating surface of the carriage includes an opening extending therethrough. A second electrical connector is mounted at least in part within the carriage and accessible via the opening in the mating surface of the carriage. When the housing is mounted to the carriage, the mating surface of the housing engages the mating surface of the carriage such that the first and second electrical connectors are operatively connected. A cable having a first end and a second end is electrically connected to the second electrical connector within the carriage at the first end of the cable. The second end of the cable is mounted within a junction box, and the junction box is mounted in a fixed positional relationship with respect to the base plate.

According to another aspect of the invention, a first and second rail may be mounted to the base plate with the second rail mounted parallel to the first rail. A carriage may be mounted between and movable along the first rail and the second rail. The first rail and the second rail each support one end of the carriage. Either the first or second rail includes a slot through which the cable passes from the carriage to the junction box. Each end of the first rail and the second rail may include a home position at which the housing may be mounted to the carriage. The mating surface of the carriage includes at, least one additional opening with a spring-biased ejector protruding through the additional opening. When the housing is removed from the carriage, the spring-biased ejector is in an unbiased state and the spring-biased ejector protrudes through the additional opening. When the housing is mounted to the carriage, the spring-biased ejector is in a biased state and the spring-biased ejector is compressed generally even to the mating surface of the carriage. The spring-biased ejector disconnects the first and second electrical connectors, separating the housing from the carriage when the carriage is moved to the home position.

According to yet another aspect of the invention, at least one of the first rail and the second rail includes a plurality of slots along an inner surface, and the carriage includes at least one tab protruding from an end of the carriage. The tab selectively engages one of the plurality of slots to retain the carriage at a position on the rail relative to the slot which the tab is engaging. At least one of the first rail and the second rail includes a plurality of indices spaced apart longitudinally along the rail, and the housing includes a positioning tab identifying one of the indices corresponding to the current location of the housing with respect to the rail.

According to still another embodiment of the invention, an antenna support structure for use during medical imaging is disclosed. The antenna support system includes a base plate, at least one rail mounted to the base plate, at least one carriage movably mounted to the at least one rail, at least one first antenna array removably mounted to the at least one carriage, and at least one second antenna array removably mounted to the base plate.

According to still another aspect of the invention, the base plate is generally planar and includes a lower surface and an upper surface. The lower surface is positionable on a table for imaging, and the upper surface has the rail mounted to it. The at least one rail may include a first rail and a second rail. Each of the first rail and the second rail are mounted to the upper surface of the base plate and spaced apart from each other, and the at least one carriage is movably mounted between the first rail and the second rail.

The antenna support structure may also include a junction box mounted to the base plate outside of the first and second rails. Either the first rail or the second rail includes a slot extending longitudinally along the rail. The at least one carriage includes an electrical cable connected between the at least one carriage, and the junction box, and the electrical cable is routed through the slot in the rail. The at least one second antenna array may include a first electrical connector, and the junction box may include a second electrical connector. The first electrical connector and the second electrical connector are connected when the at least one second antenna array is mounted to the base plate.

These and other objects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWING(S)

Various exemplary embodiments of the subject matter disclosed herein are illustrated in the accompanying drawings in which like reference numerals represent like parts throughout, and in which:

FIG. 35 is a rear elevation view of the antenna support structure as shown in FIG. 33;

FIG. 36 is a front elevation view of the antenna support structure as shown in FIG. 33;

Figure 1:
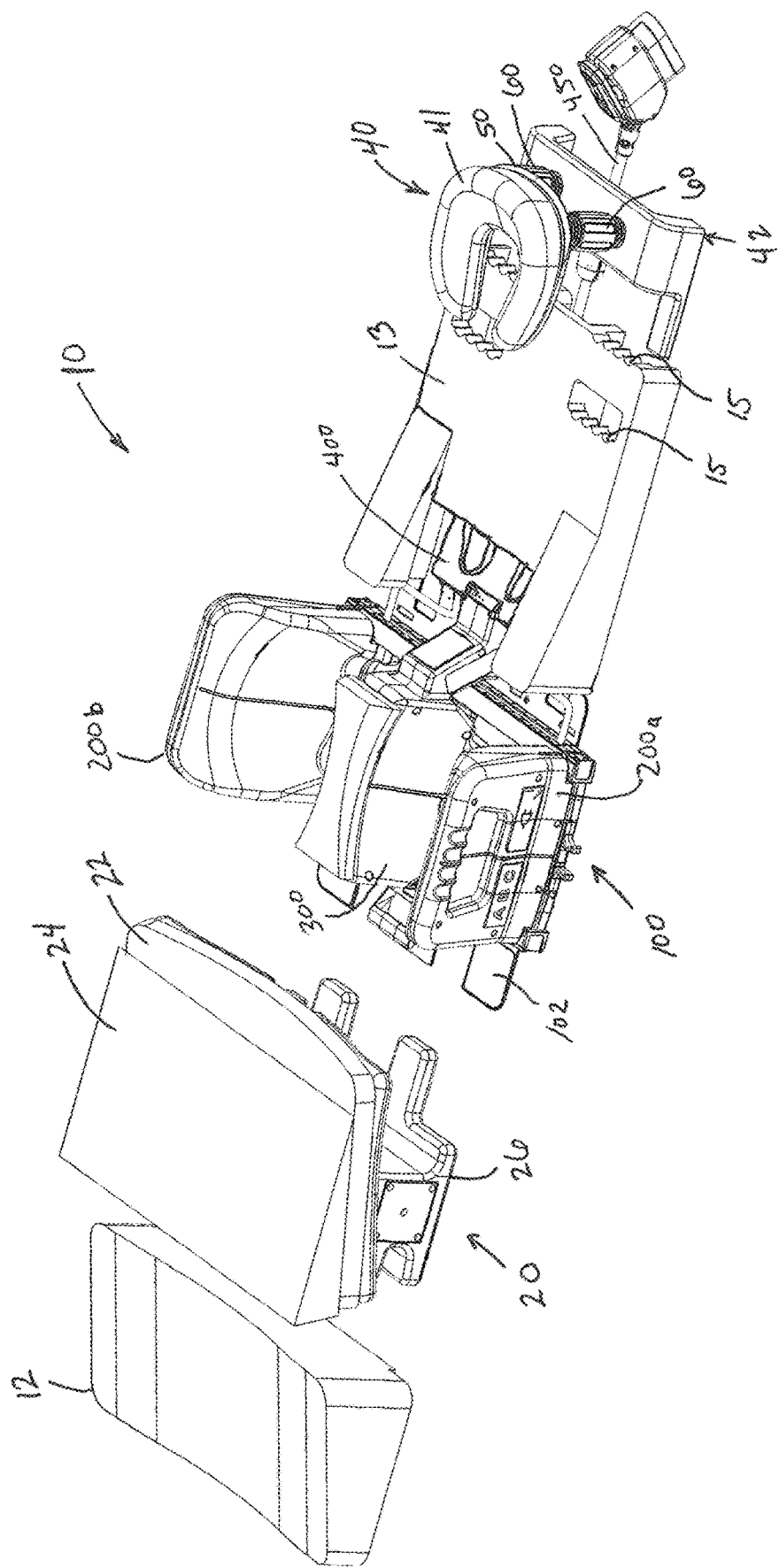
FIG. 1 is an isometric view of a magnetic resonance (MR) support and imaging system according to one embodiment of the invention.
Figure 2:
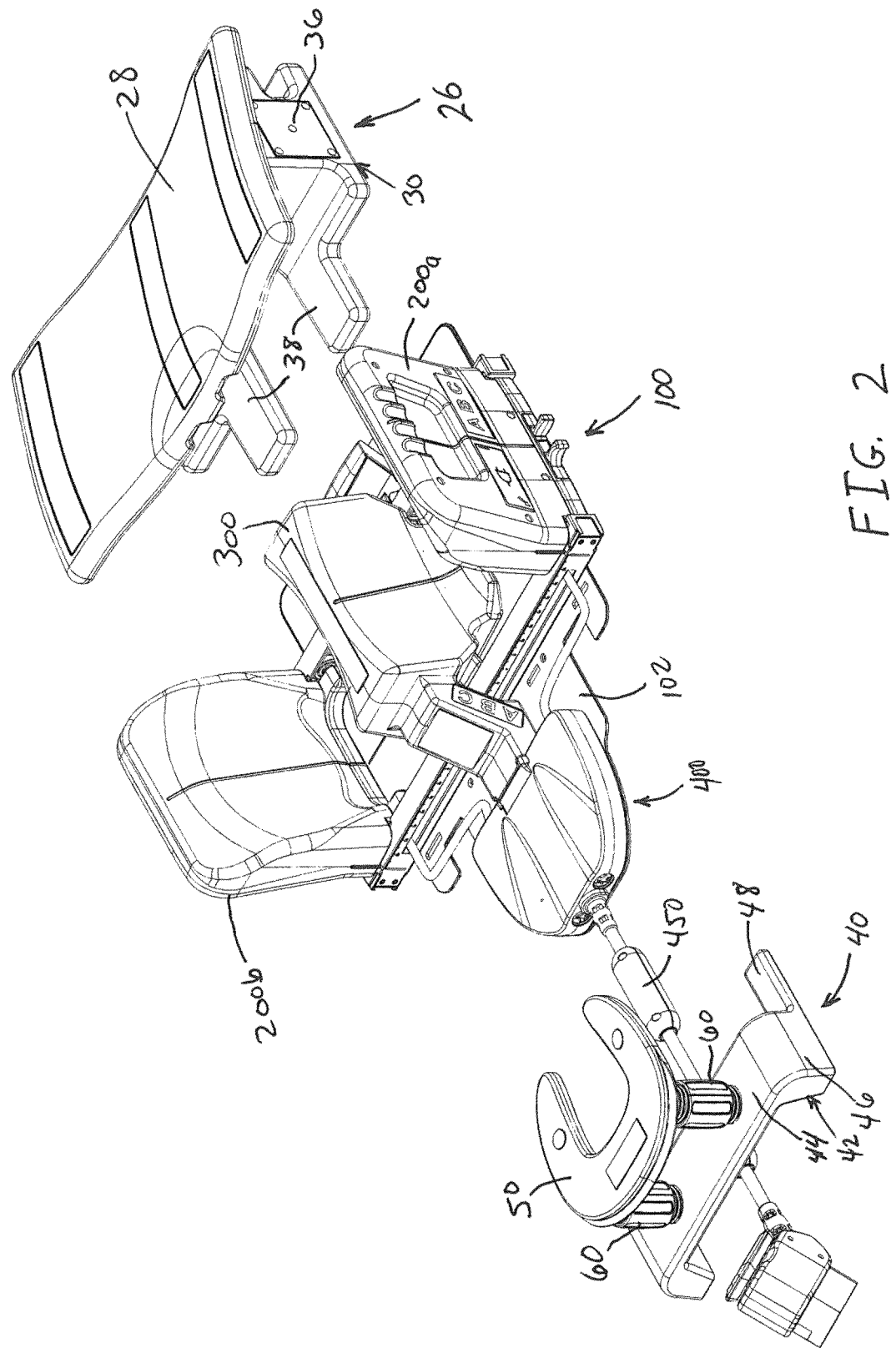
FIG. 2 is an isometric view of a portion of the MR support and imaging system of FIG. 1, illustrating the patient support structures and the antenna support structure.
Figure 3:
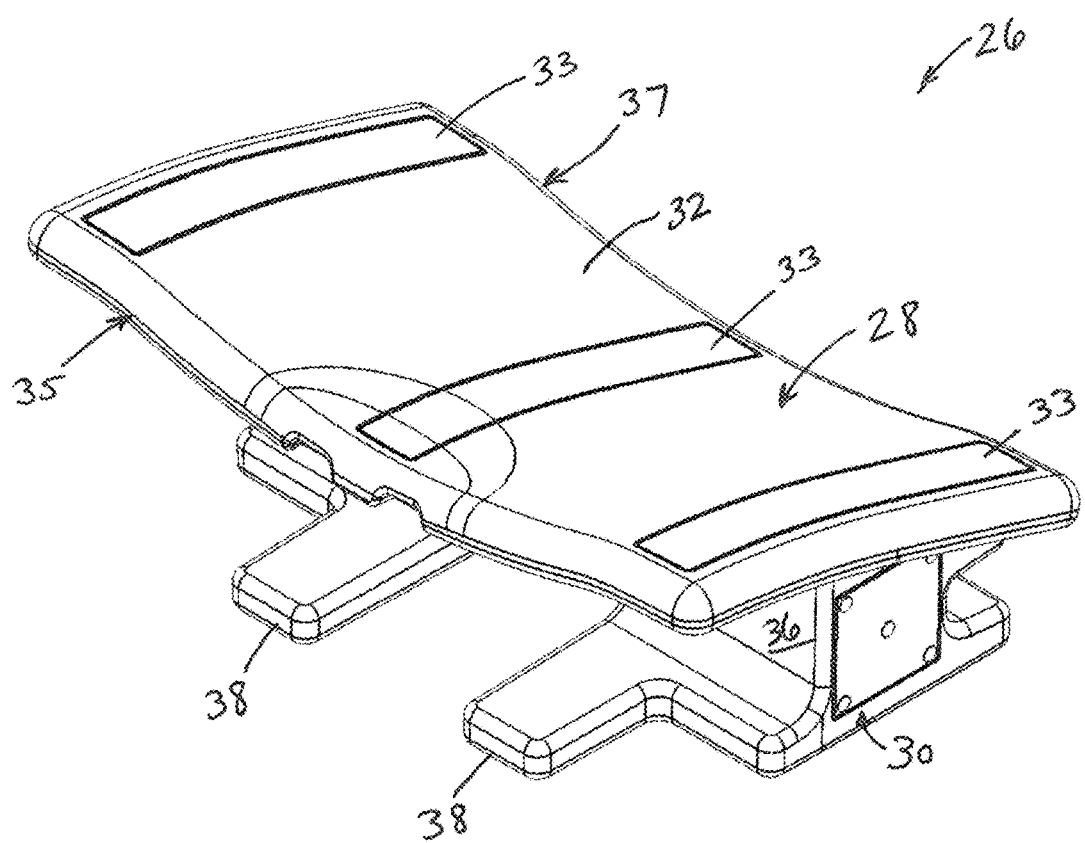
FIG. 3 is an isometric view of a first patient support member as shown in the MR support and imaging system of FIG. 1.
Figure 4:
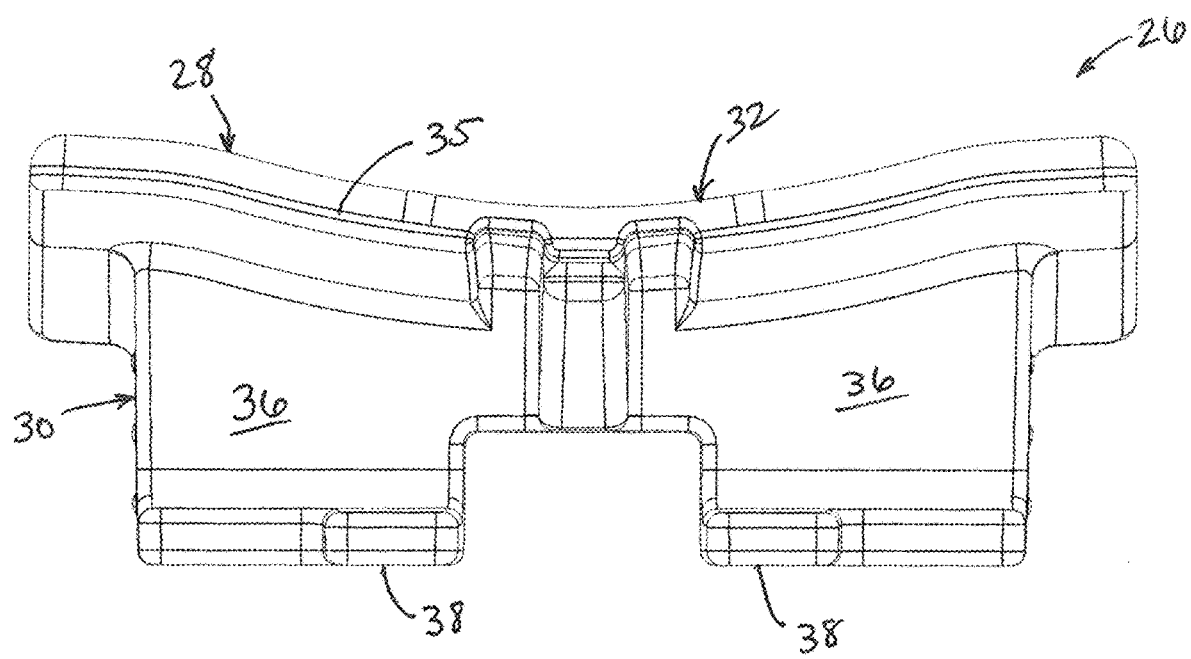
FIG. 4 is a front elevation view of the first patient support member of FIG. 3.
Figure 5:
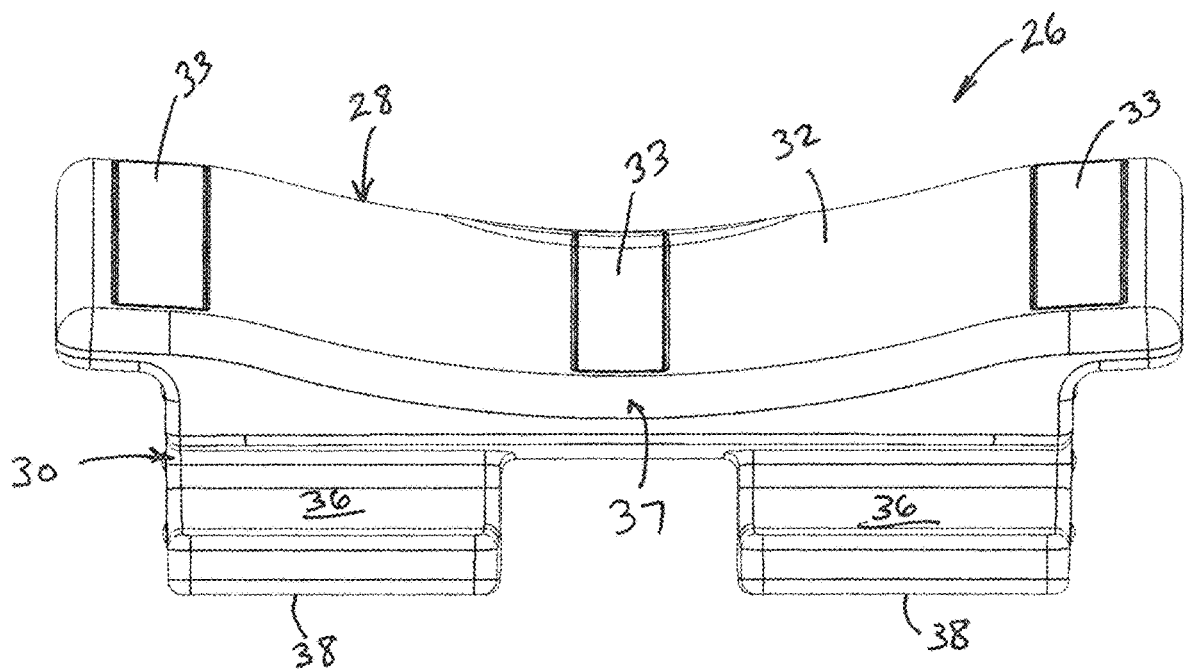
FIG. 5 is a rear elevation view of the first patient support member of FIG. 3.
Figure 6:
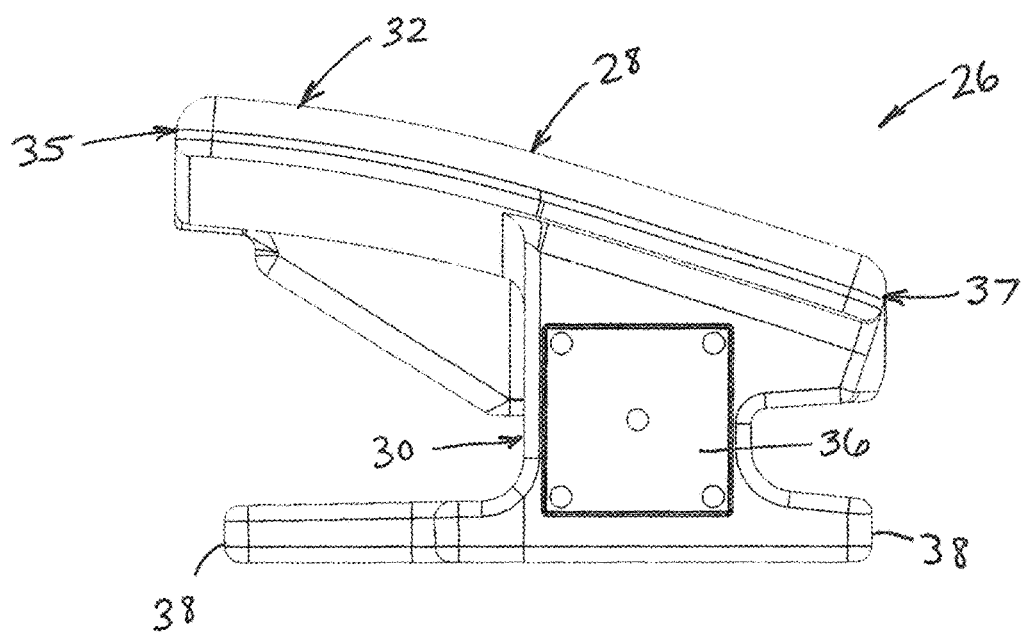
FIG. 6 is a side elevation view of the first patient support member FIG. 3.
Figure 7:
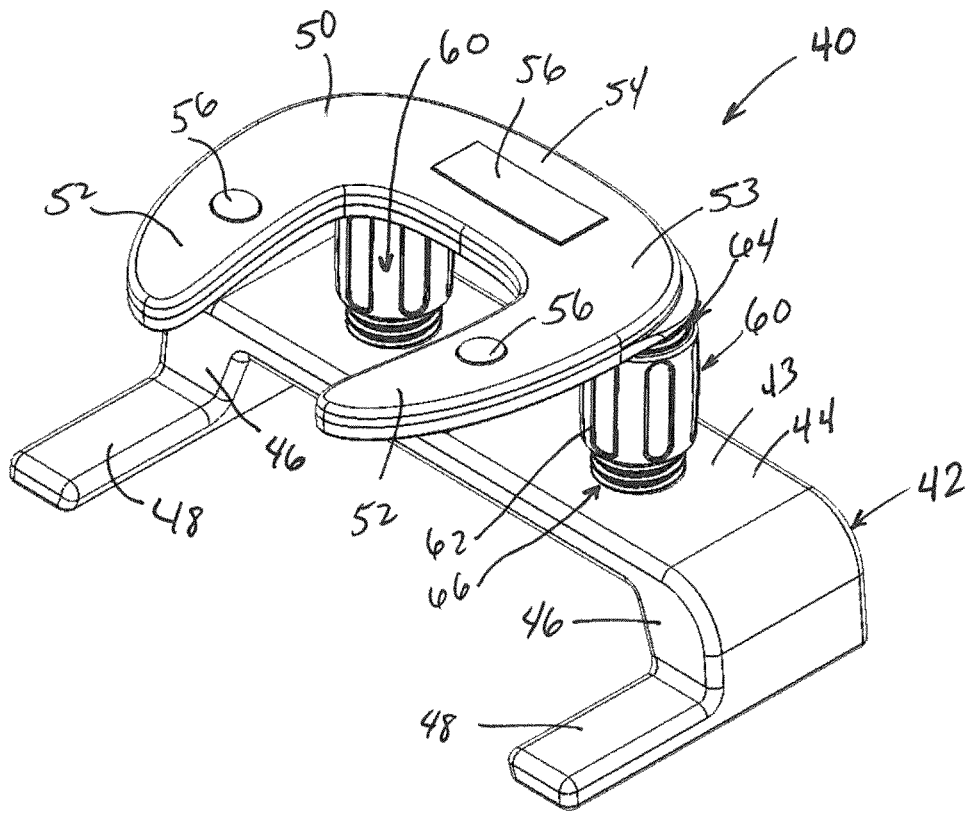
FIG. 7 is an isometric view of a second patient support member as shown in the MR support and imaging system of FIG. 1.
Figure 8:
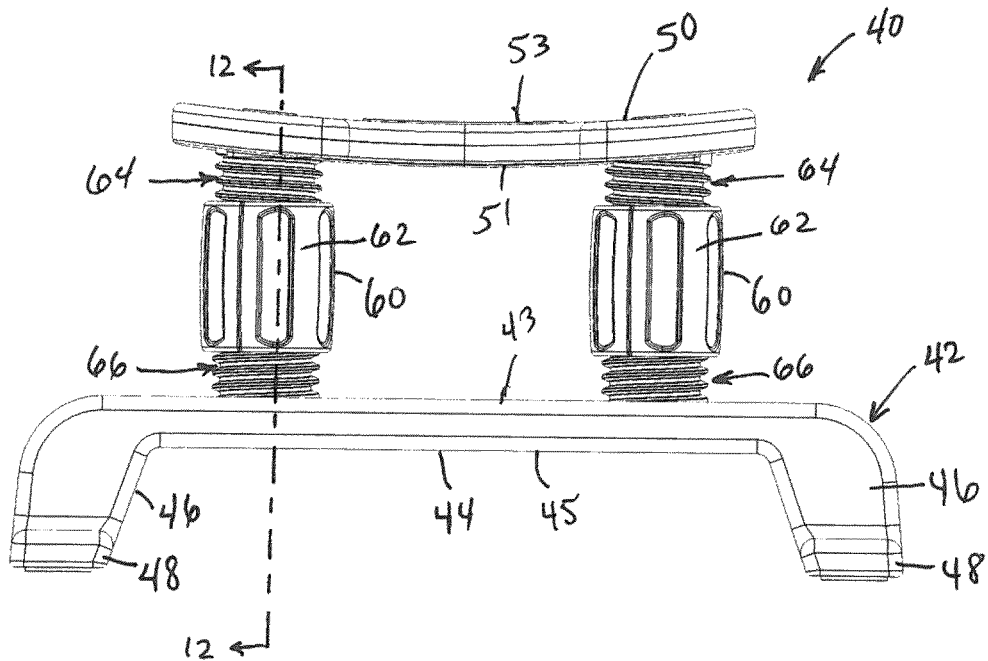
FIG. 8 is a rear elevation view of the second patient support member of FIG. 7.
Figure 9:
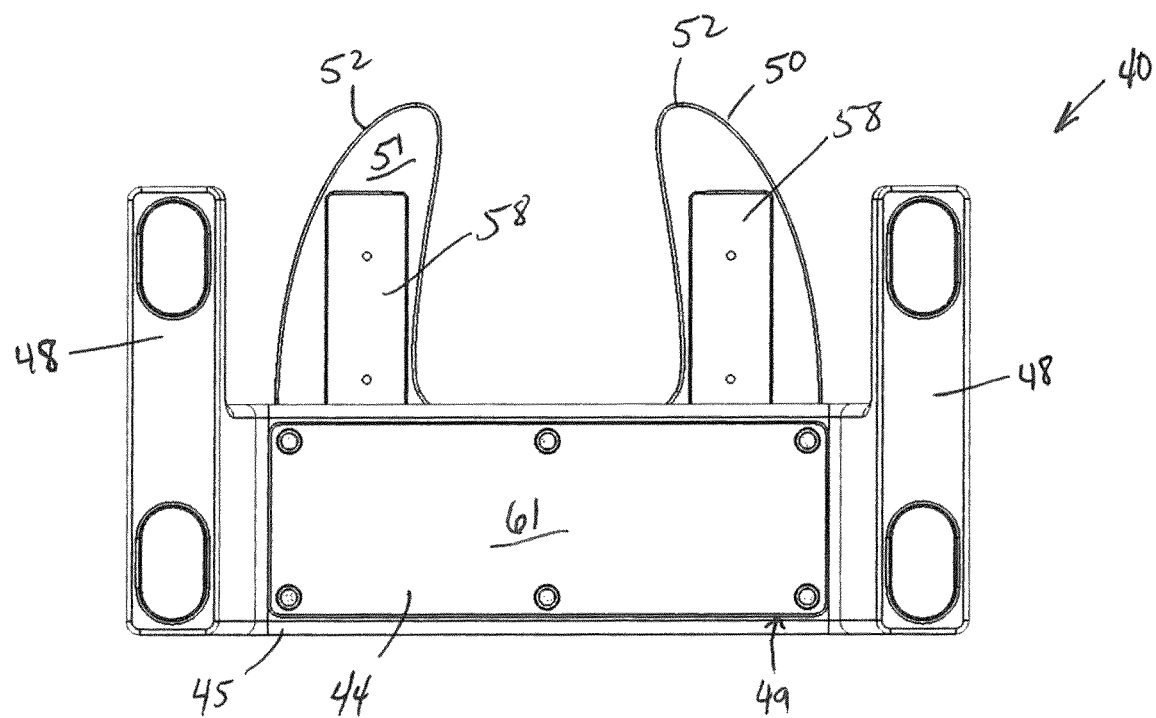
FIG. 9 is a bottom plan view of the second patient support member of FIG. 7.

In describing the preferred embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements where such connection is recognized as being equivalent by those skilled in the art.

DETAILED DESCRIPTION OF THE PREFERRED EMBODIMENTS

The various features and advantageous details of the subject matter disclosed herein are explained more fully with reference to the non-limiting embodiments described in detail in the following description.

Turning initially to FIG. 1, a magnetic resonance (MR) imaging and patient support system 10, according to one embodiment of the invention, is illustrated. The MR imaging and patient support system 10 is modular such that individual components may be positioned with respect to the patient to provide comfort and support for the patient. The MR imaging and patient support system 10 includes a first patient support structure 20, an antenna support structure 100, and a second, or head, support structure 40. The components would be placed on a surface to be inserted into a bore of an MR scanner. The surface may be, for example, a scan table connected to the MR scanner or a movable stretcher or gurney which includes a table or board which is removable from the stretcher and which may be slid into the bore of the MR scanner.

A first patient support structure 20 provides support to a lower anatomical region of the patient. According to the illustrated embodiment, the first patient support structure 20 is configured to be positioned beneath the abdomen of the patient. The patient support structure 20, includes a support member 26, a first patient support pad 22, and a second patient support pad 24. Each of the first and second patient support pads 22, 24 may have different shapes and/or different thicknesses to accommodate various size patients. Optionally, a single patient support pad may be provided. Still an additional pad 12 may be provided to provide further support extending axially along the table toward the patient's feet between the first patient support structure 20 and the table.

With reference also to FIGS. 3-6, the first patient support structure 20 includes an upper support member 28 and a lower support member 30. The upper support member 28 includes a curved surface 32 configured to receive and support the patient's abdomen. A front edge 35 of the upper support member 28 is oriented toward the patient's head, and a rear edge 37 of the upper support member 28 is oriented toward the patient's feet. The curved surface 32 may include one or more attachment strips 33 configured to engage the first support pad 22. Each of the attachment strips 33 may be of any suitable material to retain the first support pad 22 in position on the curved surface 32. For example, the attachment strip 33 may be one half of a hook and loop fastening system, and the other half of the hook and loop fastening system is secured to the bottom of the first pad 22. Optionally each attachment strip 33 may be made of a soft plastic or rubber to provide a high sliding friction surface to retain the first pad 22 in place.

Each lower support member 30 is configured to engage the table on which the patient support system 10 is located and to raise the patient a sufficient distance such that the patient's chest and breast tissue may be received in the antenna support structure 100. The lower support member 30 includes multiple feet 38 extending axially along the length of the table. Front feet 38 extend toward the front edge 35 of the upper support member 28, and rear feet 38 extend toward the rear edge 37 of the upper support member 28. The lower support member 30 includes a first leg 36 and a second leg 36. Each leg 36 includes one front foot 38 and one rear foot 38 connected to one end of the leg 36. The other end of the leg 36 is connected to the lower surface of the upper support member 28. It is contemplated that various other configurations of the first patient support structure 20 may be utilized without deviating from the scope of the invention, as long as the first patient support structure 20 engages a portion of the patient's anatomy and elevates the patient above the table a sufficient distance to engage the antenna support structure 100.

A second patient support structure 40 provides support to an upper anatomical region of the patient. According to the illustrated embodiment the second patient support structure 40 is configured to support the head of a patient. The second patient support structure includes a base 42, a head rest 50, a pair of adjustable legs 60, and a head pad 41 mounted on the head rest 50.

With reference also to FIGS. 7-12, the base 42 of the second patient support structure 40 includes a cross-member 44 and a pair of legs 46 raising the cross-member 44 up from the surface on which the MR imaging and patient support system 10 is located. The cross member 44 is a generally rectangular housing having an upper surface 43 and a lower surface 45, where each of the upper and lower surfaces 43, 45 extend between a first end and a second end, opposite the first end. A side surface extends around the periphery of the cross member 44 such that a cavity 47 is defined within the cross member 44. Each leg 46 includes an inner wall, an outer wall, a front wall, and a rear wall defining a chamber within the leg 46, where the chamber within the leg may be in communication with the cavity 47 within the cross member 44. Each leg 46 is located at one end of the cross member 44 and further includes a foot 48 protruding orthogonally to the leg 46. The foot 48 includes a lower surface, configured to rest on the surface, on which the patient support system 10 is located, an upper surface and side surfaces to similarly define a chamber within each leg 46. It is contemplated that the cross member 44, each leg 46, and each foot 48 may be a molded plastic member formed together as a single member or as multiple components joined according to any suitable method such as ultrasonic or vibration welding or by fasteners to join components.

An opening 49 extends through the lower surface 45 of the cross member 44 and is configured to receive a mounting plate 61 for the adjustable legs 60. Each adjustable leg 60 includes a turnbuckle 62 positioned between an upper threaded member 64 and a lower threaded member 66. The inner surface of the turnbuckle 62 includes a right-hand thread extending from about the middle to one end of the turnbuckle 62 and a left-hand thread extending from about the middle to the other end of the turnbuckle 62. The upper and lower threaded members 64, 66 include a complementary thread around their outer periphery such that as the turnbuckle 62 is rotated it causes both the upper and lower threaded members 64, 66 to be screwed into or out of the turnbuckle 62 in tandem.

The second patient support member 40 further includes a drive train such that when one turnbuckle 62 is rotated, the other turnbuckle 62 also rotates. The lower threaded member 66 has a passage extending axially through its center, and each leg 60 further includes a post 68 connected to the inner periphery of the turnbuckle 62 between the threaded portions such that as the turnbuckle 62 is rotated the post 68 internal to the leg 60 also rotates. The post 68 extends downward into the cavity 47 within the cross member 44, and a drive member 70 is mounted to the bottom of the post 68. According to the illustrated embodiment, the drive member 70 is a gear having a fine tooth spacing configured to engage teeth on the inner surface of a drive belt 72. The drive belt 72 is routed around the drive member 70 of both legs 60. Consequently, when the turnbuckle 62 on a first leg 60 is rotated, the post 68 within the turnbuckle 62 rotates, which, in turn, rotated the drive member 70 connected to the end of the post 68 and the drive belt 72 running around the drive member. The drive belt 72 causes the drive member 70 on the second leg 60 to rotate which, in turn, rotates the post 68 and the turnbuckle 62 of the second leg 60. Thus, when the height of the second patient support member 40 is adjusted, rotating one turnbuckle 62 causes both adjustable legs 60 to extend or retract in tandem. The adjustable legs 60 cause the head rest 50 to be raised and lowered with respect to the table on which the second patient support structure 40 is located.

The head rest 50 is a generally U-shaped member configured to provide support to a patient's head. The U-shaped member includes two arms 52 and a base member 54 joining one end of each arm 52. Specifically, the head rest 50 provides support to a patient positioned on the table in a prone position such that the patient's face is oriented downward toward the head rest 50. Each arm 52 protrudes rearward and is configured to support the side of a patient's face. The base member 54 extending 54 between each arm 52 is configured to support the forehead of a patient. The head rest 50 has an upper surface 53 and a lower surface 51. The adjustable legs 60 are mounted to the lower surface 51 proximate to the connection between each arm 52 and the base member 54. A head pad 41 may be mounted to the upper surface 53 to provide cushioning for the patient's face. The upper surface 53 may include one or more attachment locations 56 configured to engage the head pad 41. Each of the attachment locations 56 may be of any suitable material to retain the head pad 41 in position on the upper surface 53. For example, the attachment location 56 may be one half of a hook and loop fastening system, and the other half of the hook and loop fastening system is secured to the bottom of the head pad 41. Optionally each attachment location 56 may be made of a soft plastic or rubber to provide a high sliding friction surface to retain the head pad 41 in place.

Figure 10:
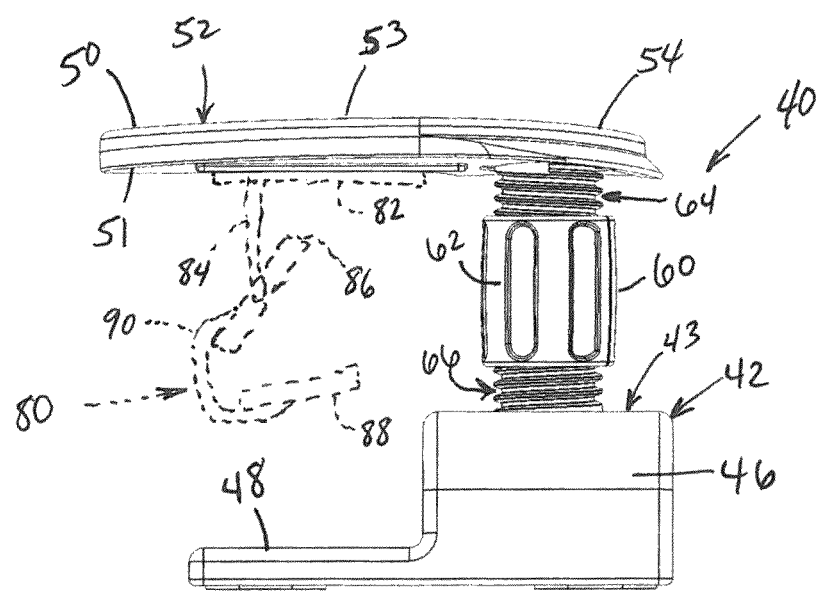
FIG. 10 is a side elevation view of the second patient support member FIG. 7.
Figure 11:
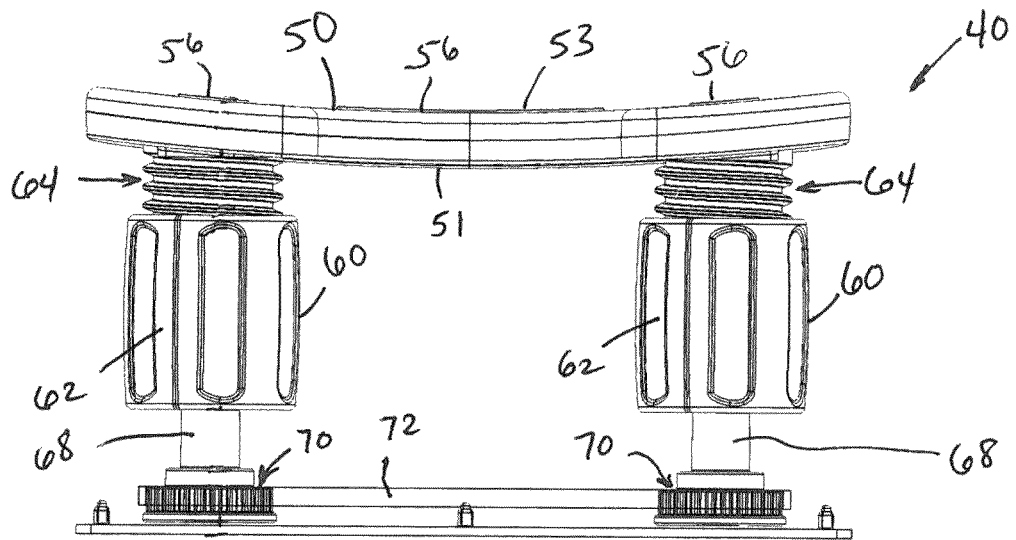
FIG. 11 is a partial rear elevation view of the second patient support member of FIG. 7 with the base removed.
Figure 12:
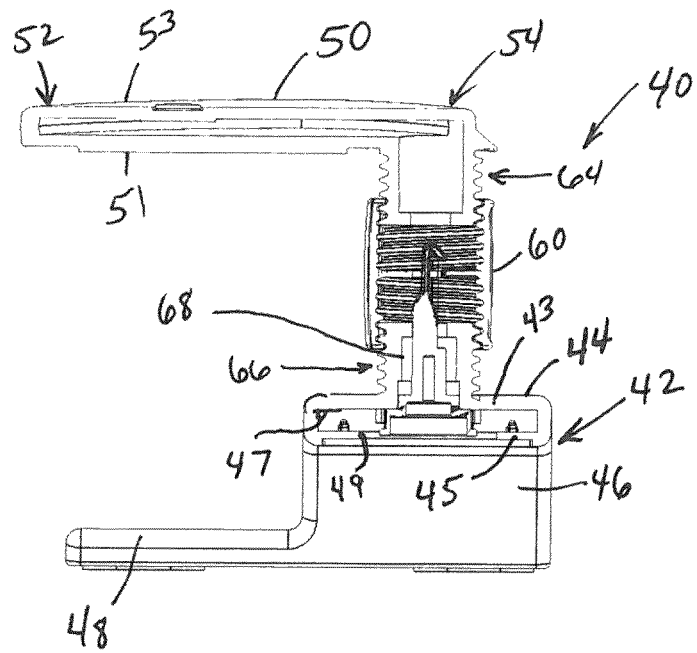
FIG. 12 is a sectional view of the second patient support member taken at 12-12 in FIG. 8.

Referring to FIG. 10, it is contemplated that the second patient support member 40 may have a mirror, assembly 80 mounted to the lower surface 51 of the head rest 50. Mounting plates 58 may be provided to which the mirror assembly 80 can be connected. A slide mechanism 82 may be mounted to each mounting plate 58 to provide adjustment of the mirror assembly forward and reverse to help align the mirror assembly 80 with the patient's eyes. An arm 84 is slidably mounted to the slide mechanism 82 and extending downward below the head rest 50. A first mirror 86 is mounted to the arm 84 and a second mirror 88 is mounted to the first mirror 86 with a second arm 90. It is contemplated that each mirror 86, 88 may be pivotally mounted to one or both arms 84, 90 to provide additional degrees of adjustment for the mirrors 86, 88 in the mirror assembly 80.

Figure 13:
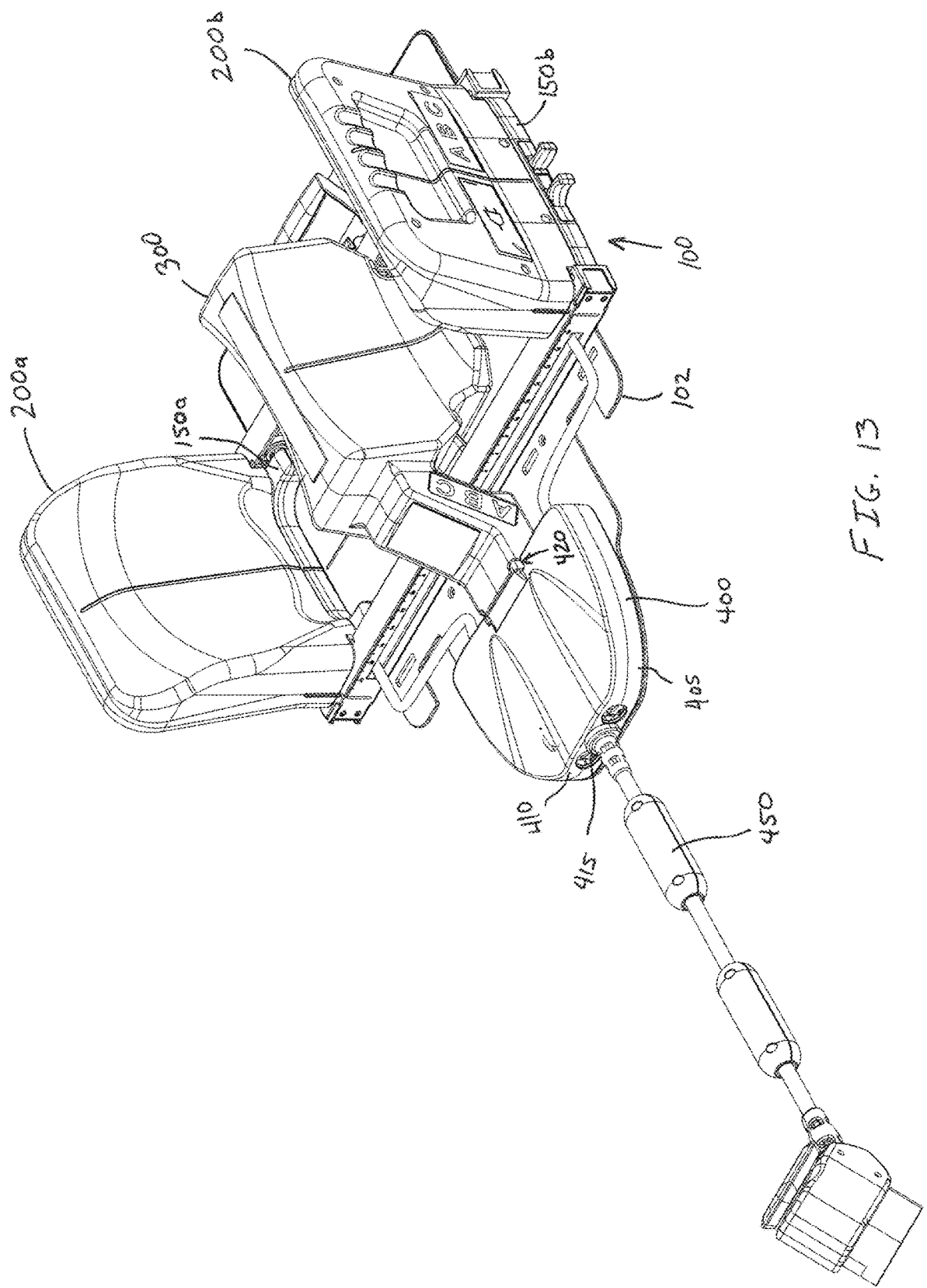
FIG. 13 is an isometric view of an antenna support structure, lateral antenna coils, medial antenna coil, junction box, and scanner cable as shown in the MR support and imaging system of FIG. 1.
Figure 14:
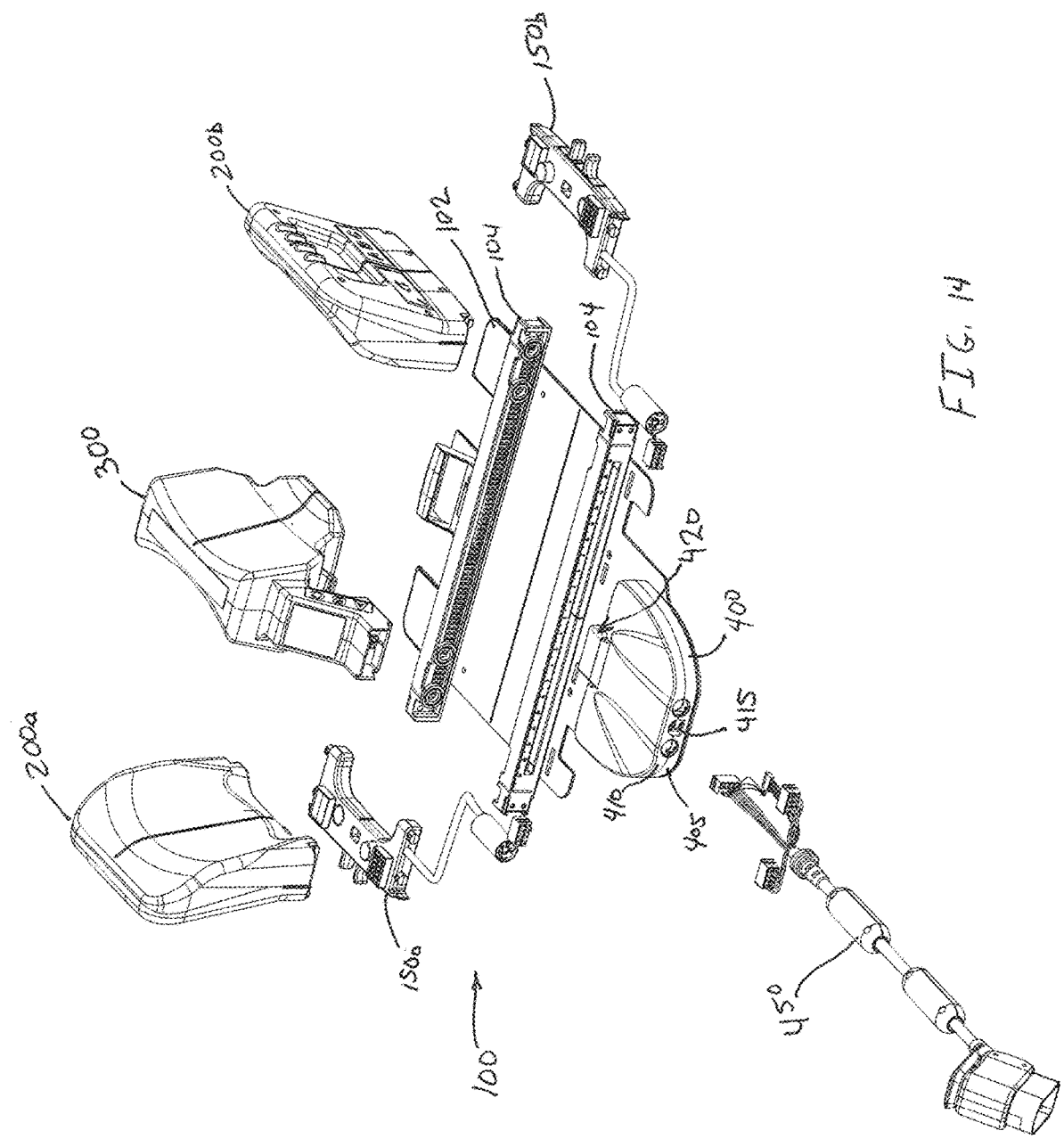
FIG. 14 is a partially exploded view of the antenna support structure, lateral antenna coils, medial antenna coil, junction box, and scanner cable of FIG. 13.
Figure 15:
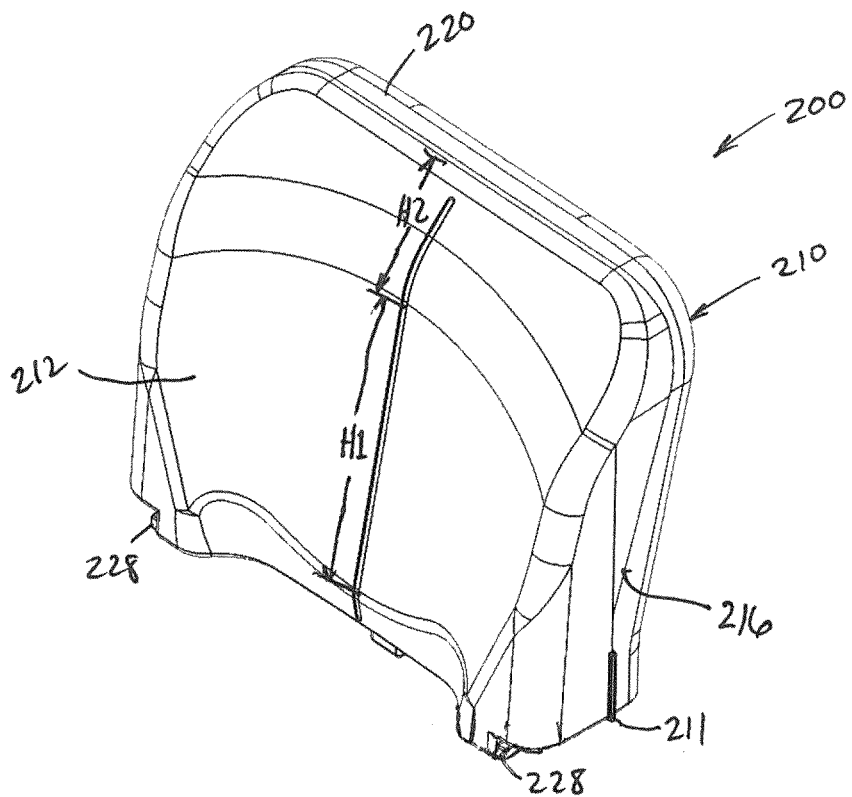
FIG. 15 is an isometric, view of a left lateral antenna array (when viewed from the rear) as shown in the MR support and imaging system of FIG. 1 from an inner side, top surface, and front side.
Figure 16:
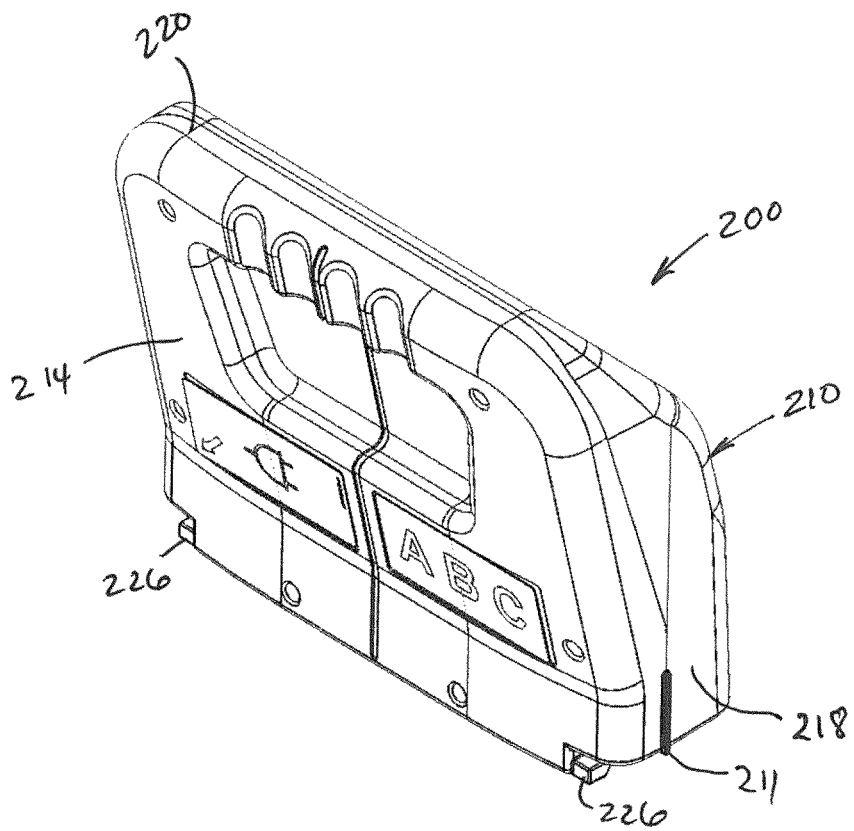
FIG. 16 is an isometric view of the left lateral antenna array of FIG. 15 from an outer side, top surface, and rear side.
Figure 17:
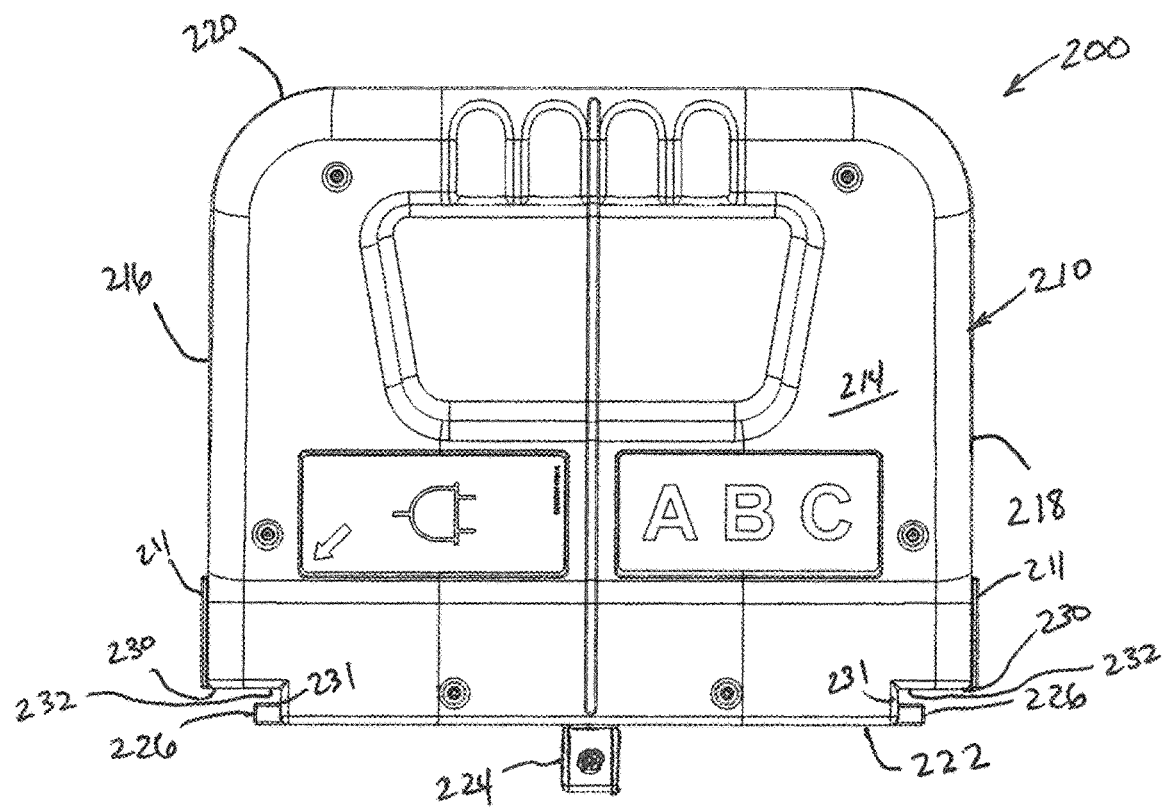
FIG. 17 is an outer surface elevation view of the left lateral antenna array of FIG. 15.

Turning next to FIGS. 13 and 14, the antenna support structure 100, antenna arrays, and components providing an electrical connection between the antenna arrays and the MR scanner are illustrated. According to the illustrated embodiment, the antenna support structure 100 has a medial antenna array 300 and two lateral antenna arrays 200 mounted thereon. Each of the antenna arrays 200, 300 is removably mounted to the antenna support structure 100. The medial antenna array 300 is centrally mounted directly to a base plate 102, and each lateral antenna array 200 is mounted to a carriage 150 which, in turn, may be moved laterally along a pair of rails 104 located on the base plate 102. The medial antenna array 300 and each carriage 150 are connected to a junction box 400. Within the junction box 400, electrical connections are established between a scanner cable 450 and each of the antenna arrays 200, 300.

It is contemplated that the antenna support structure 100 and antenna arrays 200, 300 may be configured to image either a single breast of a patient or to image both breasts of a patient in tandem. When imaging a single breast, the antenna support structure 100 may have just two antenna arrays mounted. One lateral antenna array 200 may be mounted to a carriage 150 along with either the medial lateral antenna array 300 or another lateral antenna array 200. If the medial antenna array 300 and the lateral antenna array 200 are used to image a single breast, the patient is positioned such that the breast tissue to be imaged is adjacent to the medial antenna array 300. Then the lateral antenna array 200 is positioned with respect to the medial antenna array such that the breast to be imaged is between the medial antenna array 300 and the lateral antenna array 200. If two lateral antenna arrays 200 are used, each of the lateral antenna arrays 200 may be moved along the antenna support, structure 100 and one of the two lateral antenna arrays 200 is positioned on one side and the other of the two lateral antenna arrays 200 is positioned on the other side of the breast tissue to be imaged. When both breasts of a patient are imaged in tandem, the patient is positioned with respect to the medial antenna array 300 such that one breast is on one side of the medial antenna array and the other breast is on the other side of the medial antenna array. Then each of the lateral antenna arrays 200 are positioned with respect to the medial antenna array 300 such that one breast is positioned between each of the lateral antenna arrays 200 and the medial antenna array 300.

With reference to FIGS. 15-22, a lateral antenna array 200 according to one embodiment of the invention is illustrated. The lateral antenna array 200 illustrated in these figures is the left lateral antenna array 200b. The term left is relative with respect to the orientation from which the MR imaging and patient support system 10 is being viewed and is not intended to be limiting. The right and left lateral antenna arrays 200a, 200b have substantially identical construction with some elements mirrored about a central axis of the array such that the right and left lateral antenna arrays 200a, 200b may be mounted on opposite sides of the antenna support structure 100. For convenience, only the left lateral antenna an 200b will be described in detail herein. However, the description is generally applicable to the right lateral antenna array 200a as well. The bottom surface of both the right and left lateral antenna arrays 200a, 200b are illustrated and will be discussed to illustrate a portion of the components that are mirrored about the central axis of the antenna array. Further, terms such as inner, outer, upper, lower, top, bottom, left, right, and the like will be used to describe elements of the lateral antenna arrays and other components of or connected to the antenna support structure 100. Such references are not intended to be limiting but are used solely to provide a reference with respect to other described components.

The lateral antenna array 200 includes a housing 210 substantially enclosing the antenna coils 250 within the antenna array 200. The housing 210 has an inner surface 212 configured to face toward a central axis of the antenna support structure 100 when the lateral antenna array 200 is mounted to the carriage 150 and an outer surface 214 configured to face away from the central axis of the antenna support structure 100 when the lateral antenna array 200 is mounted to the carriage 150. The housing 210 includes a front surface 216 configured to face toward the second patient support structure 40 when the lateral antenna array 200 is mounted to the carriage 150 and a rear surface 218 configured to face toward the first patient support structure 20 when the lateral antenna array 200 is mounted to the carriage 150. The housing further includes a top surface 220 distal from the carriage 150 when the lateral antenna array 200 is mounted to the carriage 150 and a bottom surface 222 adjacent to the carriage 150 when the lateral antenna array 200 is mounted to the carriage 150.

Figure 18:
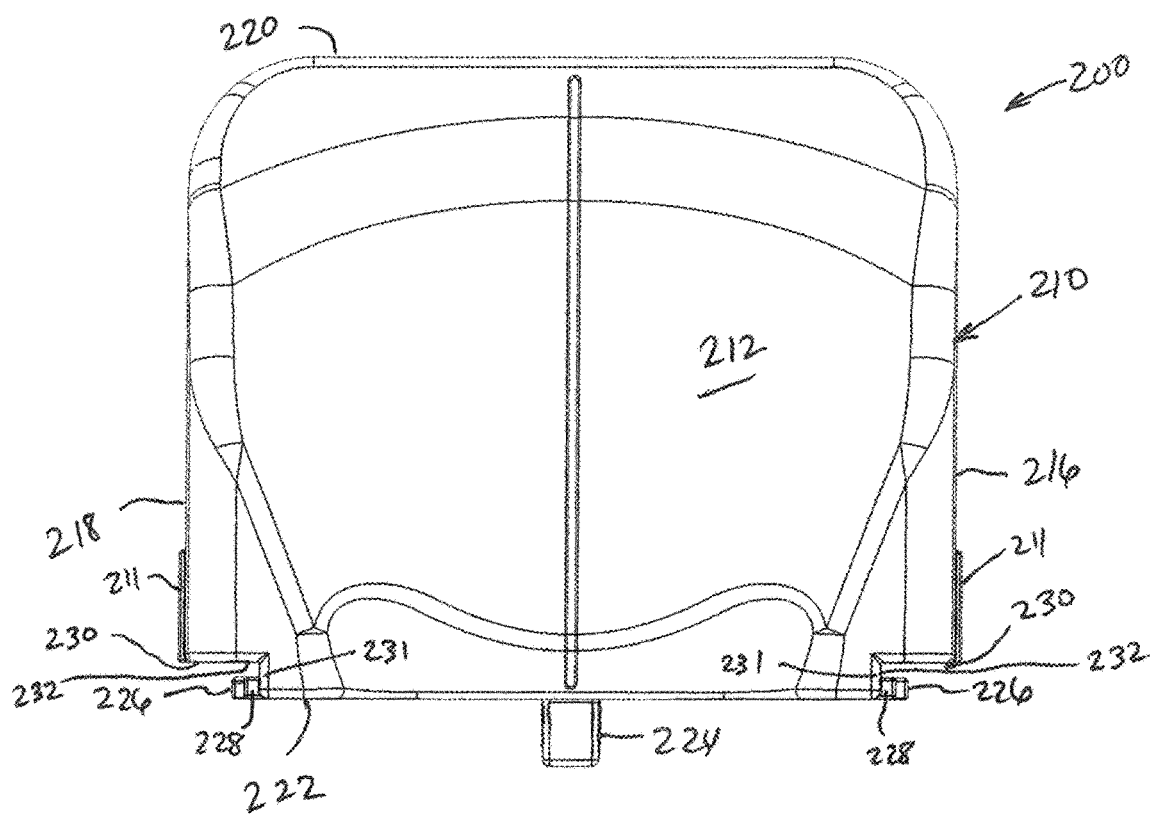
FIG. 18 is an inner surface elevation view of the left lateral antenna array of FIG. 15.
Figure 19:
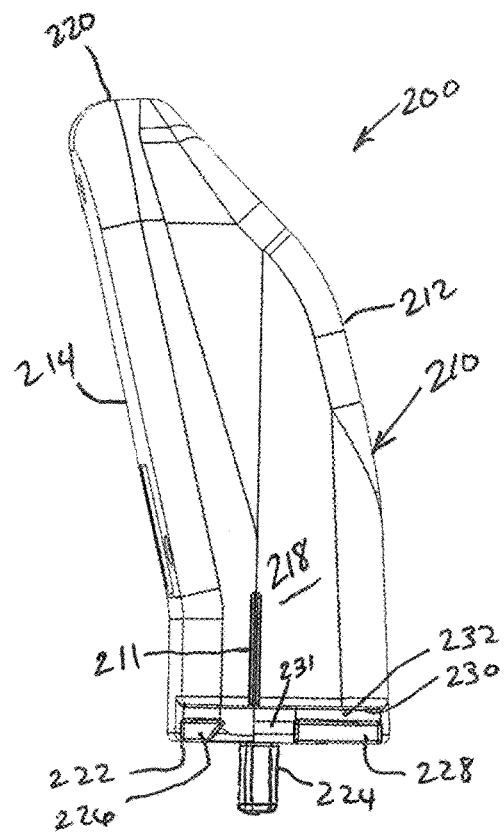
FIG. 19 is a rear elevation view of the left lateral antenna array of FIG. 15.
Figure 20:
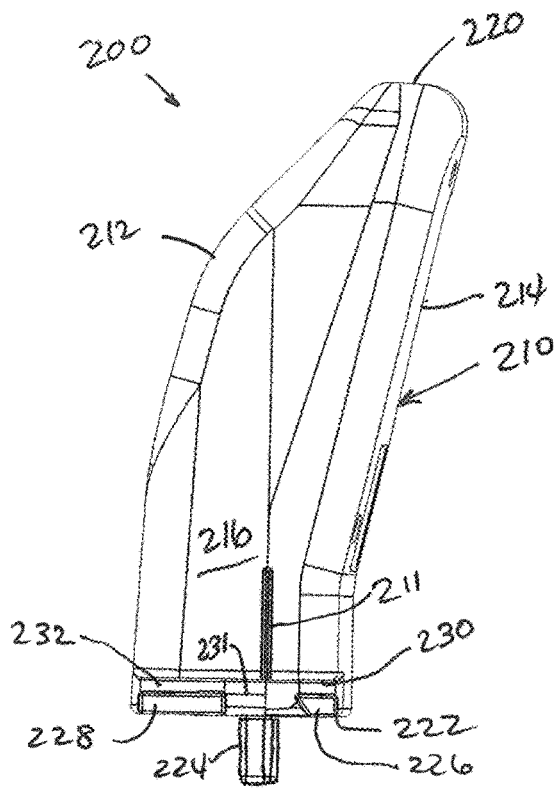
FIG. 20 is a front elevation view of the left lateral antenna array of FIG. 15.
Figure 21:
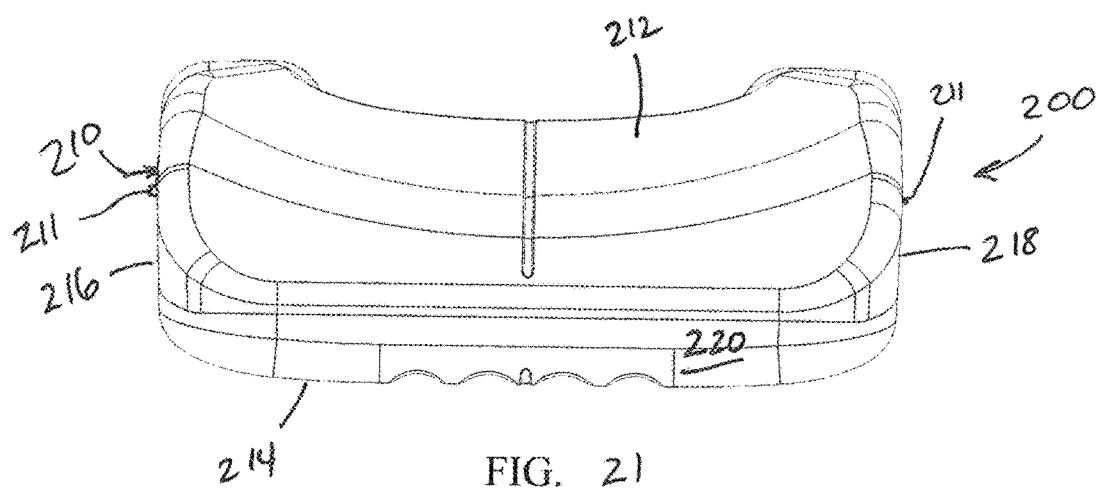
FIG. 21 is a top surface plan view of the left lateral antenna array of FIG. 15.
Figure 22:
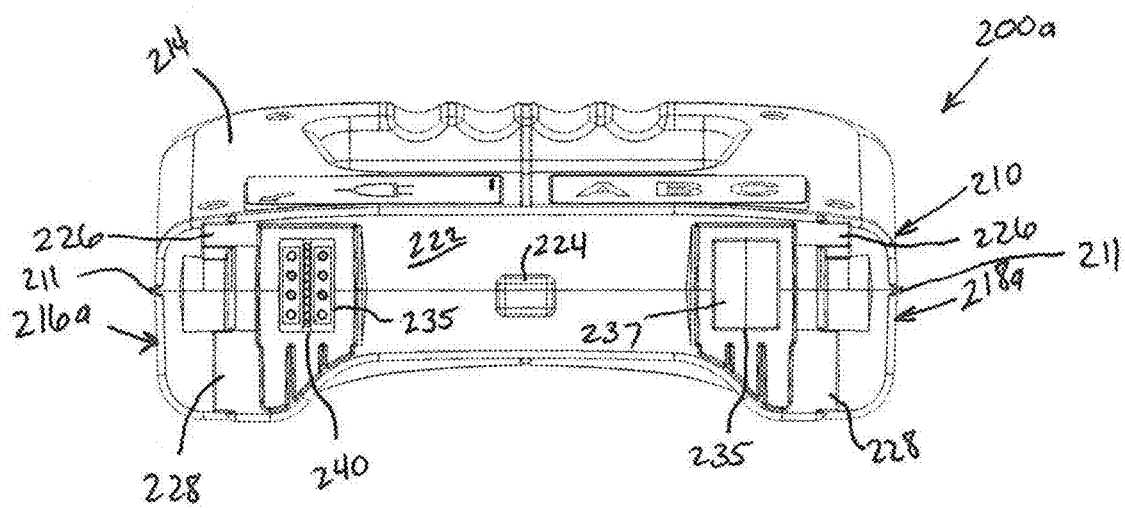
FIG. 22 is a bottom surface plan view of the left lateral antenna array of FIG. 15.

The housing 210 is configured to allow the lateral antenna array 200 to be removably mounted to the carriage 150. With reference in particular to FIGS. 18 and 22, the lateral antenna array 200 has a boss 224 protruding downward from the bottom surface 222 and configured to engage an opening 170 in the carriage 150. The boss 224 and opening 170 help position the lateral antenna array 200 with respect to the carriage 150 as it is mounted to the carriage 150. The bottom surface 222 also includes a pair of recessed segments 230 located at each of the outer sides. A first recessed segment 230 is proximate the front side 216 of the housing, and a second recessed segment 230 is proximate the rear side 218 of the housing. Each recessed segment 230 is generally parallel to and offset from the portion of the bottom surface 222 that is adjacent to the carriage 150. A short wall 231 joins the bottom surface 222 to each of the recessed segments 230. A first tab 226 and a second tab 228 each protrudes generally orthogonally from and along each of the short walls 231. An outer surface of each of the first tab 226 and the second tab 228 is generally coplanar with the bottom surface 222 and an inner surface of each of the first tab 226 and the second tab 228 is located between the bottom surface 222 and a surface of the recessed segment 230 such that a channel 232 is defined between the inner surface of the tabs 226, 228 and the surface of the recessed segment 230. The tabs 226, 228 are complementary to cutouts 107 in the top surface 106 of one of the rails 104 on the antenna support structure 100 and the channel. 232 is configured to engage the top surface of the rails 104, as will be discussed in more detail below.

The inner surface 212 of each housing 210 is configured to engage the patient during MR imaging. According to a preferred embodiment, the inner surface 212 is configured to engage breast tissue of a patient as the patient is supported by the first and second patient support structures 20, 40. The inner surface 212 includes a concave curvature between the front side 216 and the rear side 218 to accept the curvature of breast tissue. In addition, the inner surface 212 is sloped outward at a generally constant slope from the bottom surface 222 and extending up for a first height, H1, of the total height of the housing 210. The inner surface 212 then curves backward at an increasing slope for a second height, H2, of the total height of the housing. The sloped surface allows the inner surface 212 to better conform to breast tissue than a vertical surface because the breast tissue typically has a greater diameter proximate the chest cavity and a lesser diameter as it extends from the chest cavity. The curvature and increased slope along the second height, H2 of the inner surface 212 better accommodates the axilla tissue and the chest region proximate the patient's arm. Thus, the shape of the inner surface provides for improved patient comfort and for an improved coverage of the breast tissue during imaging.

Figure 24:
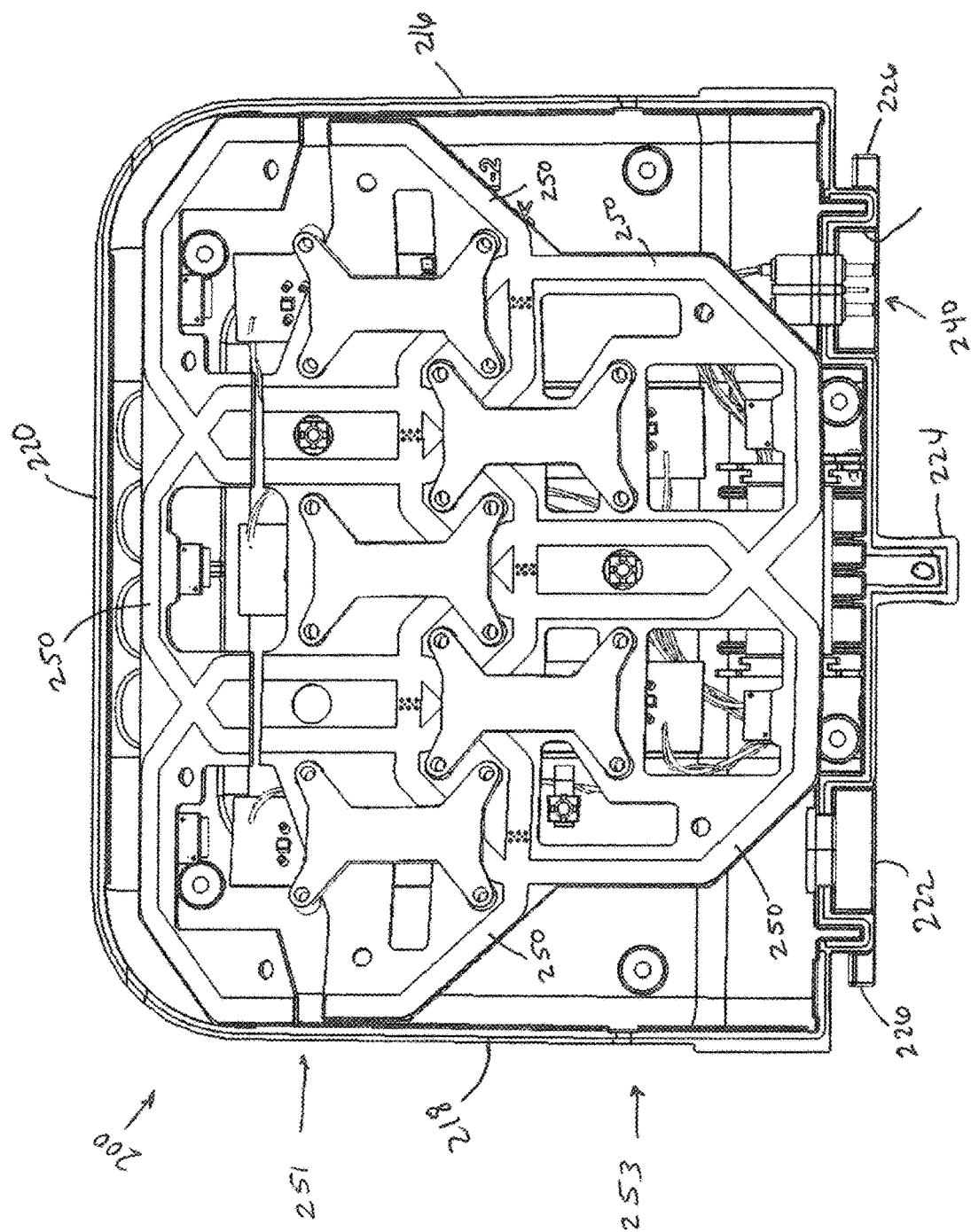
FIG. 24 is a partial schematic view of the antenna coils within the left lateral antenna array of FIG. 15 with the inner surface of the housing removed.
Figure 25:
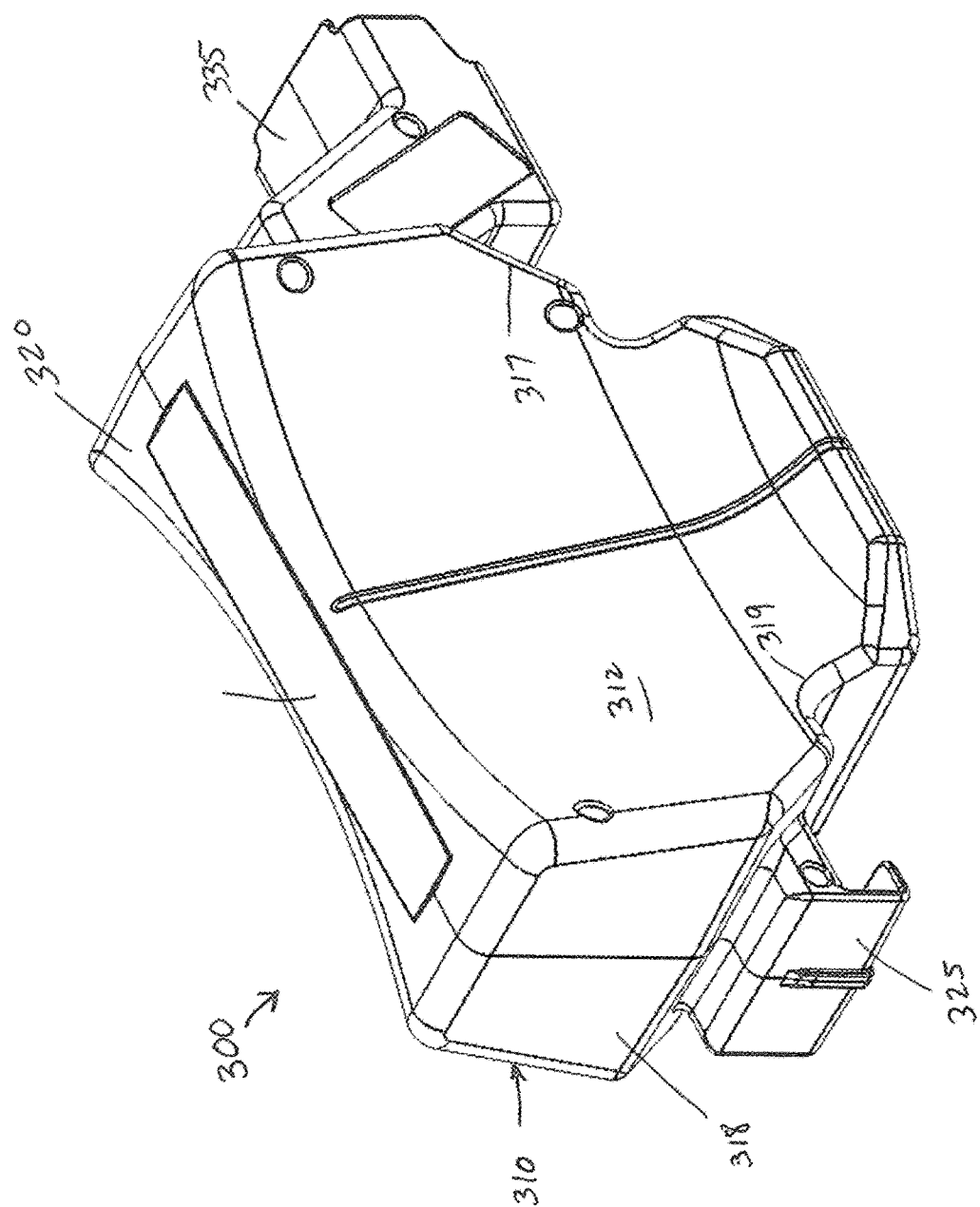
FIG. 25 is an isometric view of a medial antenna array as shown in the MR support and imaging system of FIG. 1 from a right, top, and front surface.
Figure 26:
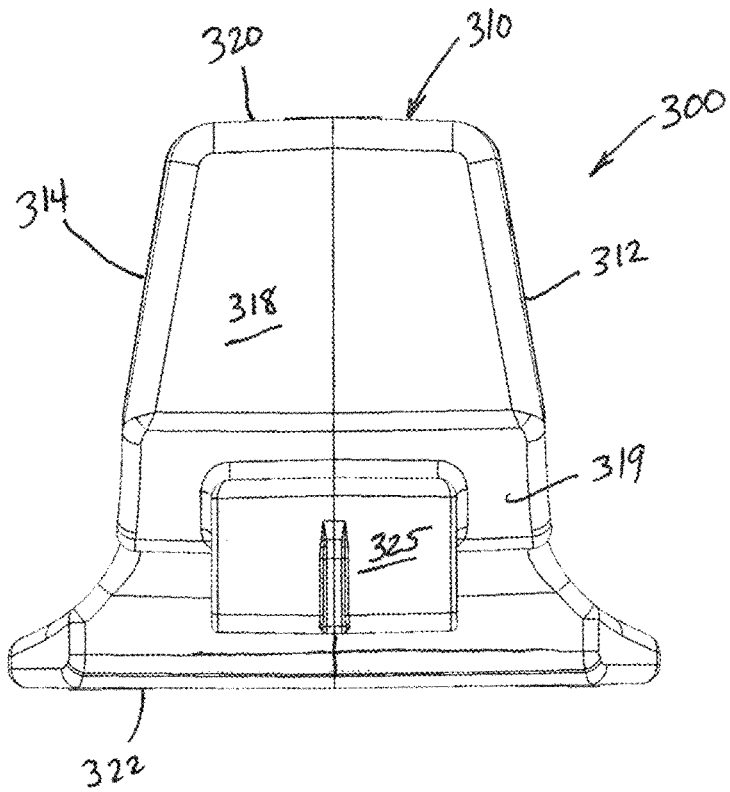
FIG. 26 is a rear elevation view of the medial antenna array of FIG. 25.

Turning next to FIG. 24, the arrangement of the antenna coils 250 further provides for improved coverage of the breast tissue during imaging. Each of the lateral antenna arrays 200 includes five antenna coils 250 located within the array 200. A first row 251 of coils 250 having three coils 250 extends between the front and rear sides 216, 218 and along the top side 220 of the array 200. A second row 253 of coils 250 having two coils 250 extends between the front and rear sides 216, 218 and along the bottom side 222 of the array 200. Because the volume of breast tissue located proximate the top side 220 of the array 200, which will be located proximate the chest of the patient during imaging, is greater than the volume of breast tissue located proximate the bottom side 222 of the antenna array 200 which is distal from the patient's chest, the higher number of coils 250 along the top side 220 provides increased coverage of the breast tissue during imaging. The configuration of coils 250 also reduces scan times in both the anterior/posterior and superior/inferior directions.

Figure 23:
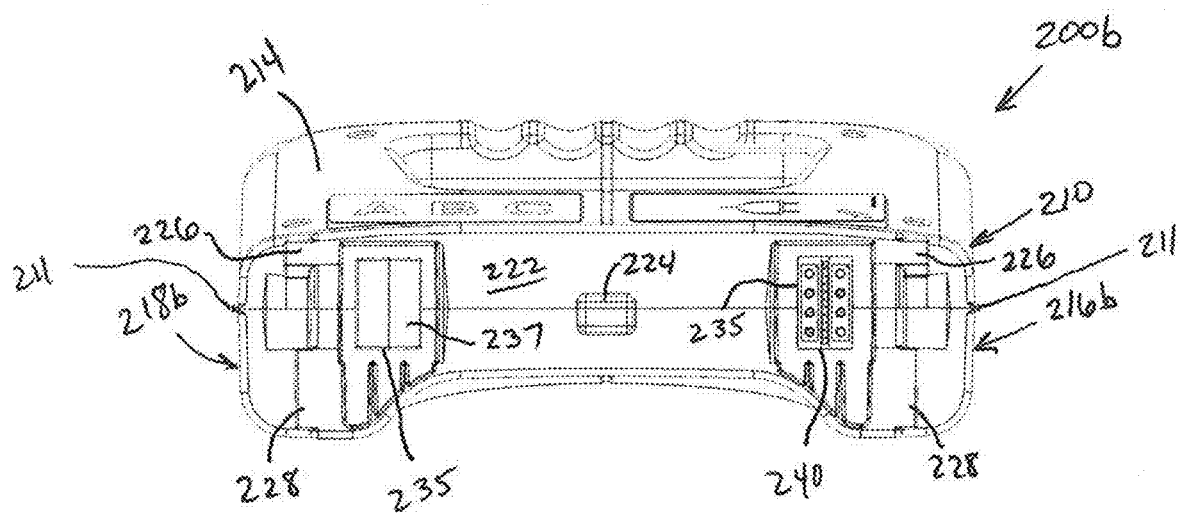
FIG. 23 is a bottom surface plan view of a right lateral antenna array as shown in the MR support and imaging system of FIG. 1.

Referring back to FIGS. 22 and 23, an electrical connector 240 positioned on the bottom surface 222 provides power to the antenna array 200 and transmits the NMR signals detected by the antenna coils 250 to the MR scanner. A pair of openings 235 is formed in the bottom surface 222 to receive the electrical connector 240. As previously indicated, at least a portion of the components within a right lateral antenna array 200a may be located within the array 200 in a position that is mirrored about a central axis of the array 200 with respect to the left lateral antenna array 200b. Thus, a first opening 235 is located proximate the front surface 216 of the antenna array 200, and a second opening 235 is located proximate the rear surface 218 of the antenna array 200.

Although the same housing 210 is used for each of the right and left antenna arrays 200a, 200b it is desirable that the connector 240 extend through the opening 235 located toward the front surface 216 of the respective housing 210. When an antenna array 200 is mounted to the left side of the antenna support structure 100 and is designated as the left antenna array 200b, as illustrated in FIGS. 15-22, the front surface 216a and rear surface 218a correspond to the front and rear surfaces 216, 218 discussed above. When an antenna array 200 is mounted to the right side of the antenna support structure 100 and is designated as the right antenna array 200a, as illustrated in FIGS. 13-14, the array must be rotated about the central axis with respect to the left antenna array 200b such that the inner surface 212 remains directed toward the center of the antenna support structure 100. As a result of the rotation, the front surface 216a of the array, when mounted as a left antenna array 200b, becomes the rear surface 218a of the array when mounted as a right antenna array 200a and the rear surface 218a of the array, when mounted as a left antenna array 200b, becomes the front surface 216a of the array when mounted as a right antenna array 200a. The connector 240 is positioned within the opening 235 proximate to the front surface 216a, 216b of the respective array 200a, 200b and a cover 237 is placed over the opening 235 proximate to the rear surface 218a, 218b of the respective array 200a, 200b.

Turning next to FIGS. 25-32, a medial antenna array 300 according to one embodiment of the invention is illustrated. The medial antenna array 300 includes a housing 310 substantially enclosing the antenna coils 350 within the medial antenna array 300. The housing 310 has a right surface 312 configured to face toward a right side of the antenna support structure 100 and a left surface 314 configured to face toward a left side of the antenna support structure 100. The housing includes a top surface 320 distal from the antenna support structure 100 and a bottom surface 322 adjacent to the base plate 102 when the medial antenna array 300 is mounted to the antenna support structure. The housing 310 further includes a front surface 316 configured to face toward the second patient support structure 40 when the medial antenna array 300 is mounted to the antenna support structure 100 and a rear surface 318 configured to face toward the first patient support structure 20 when the medial antenna array 300 is mounted to the antenna support structure 100. Each of the front and rear surface 316, 318 are generally planar and are proximate the top surface 320 of the housing 310. Each of the front and rear surfaces 316, 318 extend downward for a first portion of the height of the housing 310. A front beveled surface 317 joins the bottom edge of the front surface 316 and extends downward and to the rear of the housing 310. The front beveled surface 317 extends between the bottom edge of the front surface 316 and the bottom surface 322. A rear beveled surface 319 joins the bottom edge of the rear surface 318 and extends downward and to the front of the housing 310. The rear beveled surface 319 extends between the bottom edge of the rear surface 318 and the bottom surface 322.

The housing 310 is configured to allow the medial antenna array 300 to be removably mounted to the antenna support structure 100. A c-shaped hook 325 extends outward from the rear beveled surface 319. The hook 325 includes a first and second horizontal member and a vertical member joining the two horizontal members, defining a channel 327 within the hook 325. The channel 327 is configured to engage the rear rail 104 of the antenna support structure 100. The rear beveled surface 319 further includes, a recessed segment such that a lower wall 321 which is generally orthogonal to the bottom surface 322 is defined. The lower wall 321 extends upward from the bottom surface for a distance generally equal to the point at which the hook 325 protrudes from the beveled surface. Thus, the channel 327 and that lower wall 321 define a space in which the rear rail 104 may be received. Similarly, the front beveled surface 317 includes a recessed segment such that a lower wall 315 which is generally orthogonal to the bottom surface 322 is defined. The lower wall 315 extends upward from the bottom surface for a distance generally equal to the lower wall 321 on the rear beveled surface 319. A boss 330 protrudes from the front lower wall 315 a distance such that the front edge 331 of the boss 330 engages the front rail 104. The front surface 316 also has a connection arm 335 extending forward and downward from the front surface 316. The connection arm 335 includes a first angled portion having a front surface 336 and a rear surface 338 and a lower horizontal portion having a top surface 340 and a bottom surface 342. The bottom surface 342 of the horizontal portion of the connection arm 335 is coplanar to the bottom surface 322 of the housing such that both may be positioned on the base plate 102. The angled portion of the connection arm 335 allows the connection arm 335 to extend over the front rail 104. A rear surface 341 of the lower horizontal portion is spaced apart from the front edge 331 of the boss 330 a sufficient distance to allow the front rail 104 to be received therebetween.

The right and left surfaces 312, 314 of each housing 310 is configured to engage the patient during MR imaging. Each of the right and left surfaces 312, 314 includes a concave curvature between the front surface 316 and the rear surface 318 of the housing 310. In addition, the right and left surfaces 312, 314 are each sloped inward from the bottom surface 322 toward the top surface 320. Similar to the housing 210 on the lateral antenna arrays 200, the sloped surfaces on the housing 310 for the medial antenna array 300 allows the right and left surfaces 312, 314 to better conform to breast tissue than a vertical surface because the breast tissue typically has a greater diameter proximate the chest cavity and a lesser diameter as it extends from the chest cavity.

Figure 32:
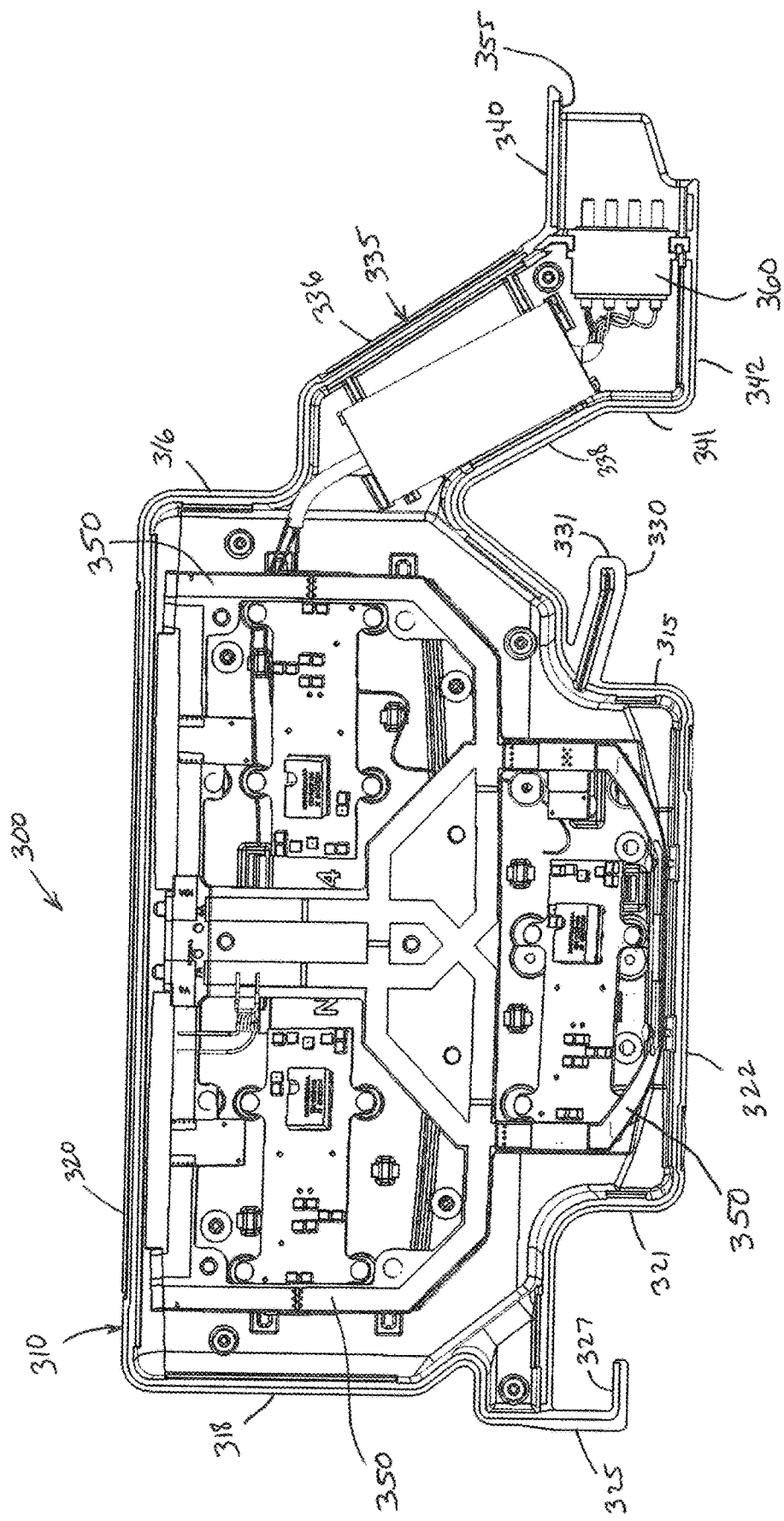
FIG. 32 is a partial schematic view of one of the right set of antenna coils within the medial antenna array of FIG. 25 with the right surface of the housing removed.

With reference also to FIG. 32, the arrangement of the antenna coils 350 further provides for improved coverage of the breast tissue during imaging. Each side of the medial antenna array 300 includes three antenna coils 350. Two antenna coils 350 are positioned along the upper surface 320 and one antenna coil 350 is positioned along the bottom surface 322. A first set of three antenna coils 350 works in conjunction with the right lateral antenna array 200a and a second set of three antenna coils 350 works in conjunction with the left lateral antenna array 200b. Each set of coils 350 on one side is decoupled from the set of coils 350 on the other side of the medial antenna array utilizing appropriate capacitive or inductive decoupling techniques. Because the volume of breast tissue located proximate the top side 320 of the array 300, which will be located proximate the chest of the patient during imaging, is greater than the volume of breast tissue located proximate the bottom side 322 of the antenna array 300 which is distal from the patient's chest, the higher number of coils 350 along the top side 320 provides increased coverage of the breast tissue during imaging. The configuration of coils 350 also reduces scan times in both the anterior/posterior and superior/inferior directions.

Figure 27:
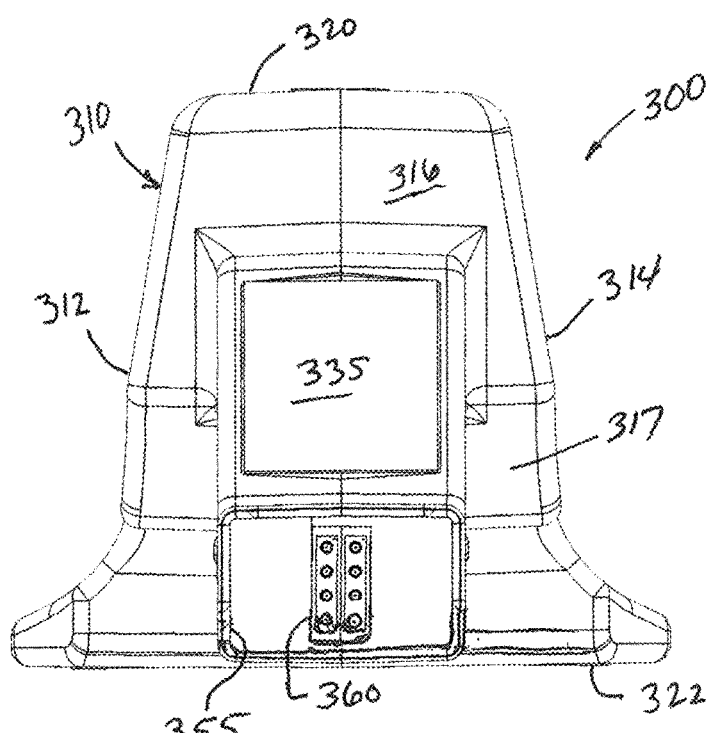
FIG. 27 is a front elevation view of the medial antenna array of FIG. 25.
Figure 28:
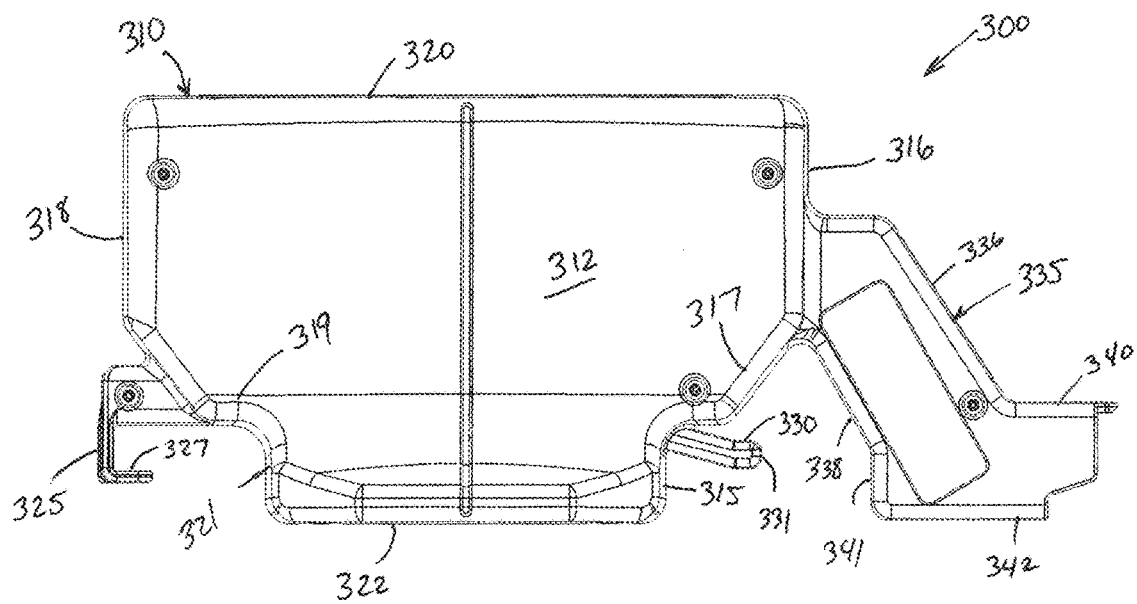
FIG. 28 is a right surface elevation view of the medial antenna array of FIG. 25.
Figure 29:
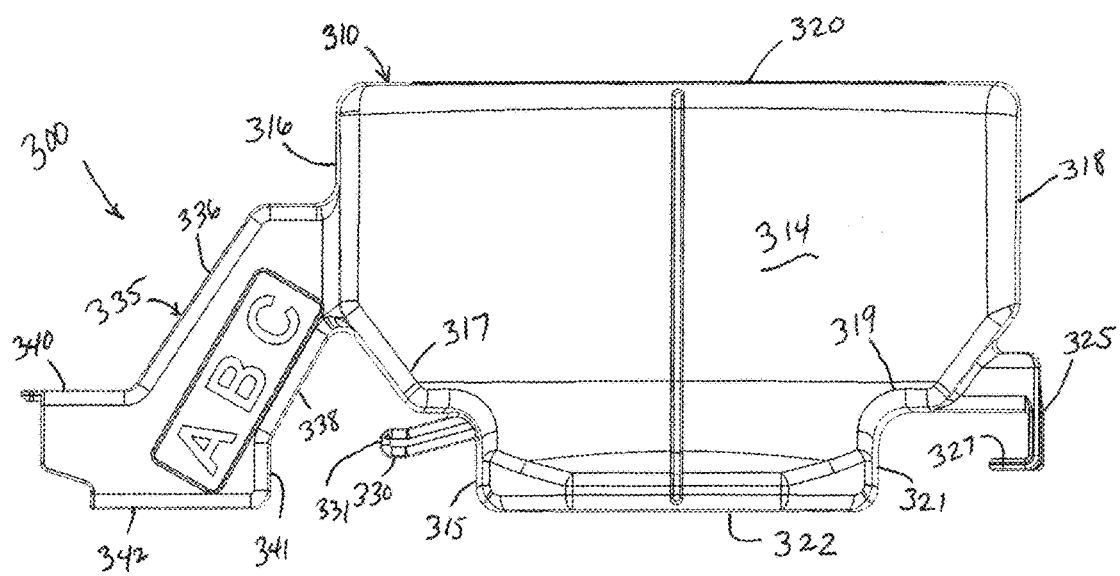
FIG. 29 is a left surface elevation view of the medial antenna array of FIG. 25.
Figure 30:
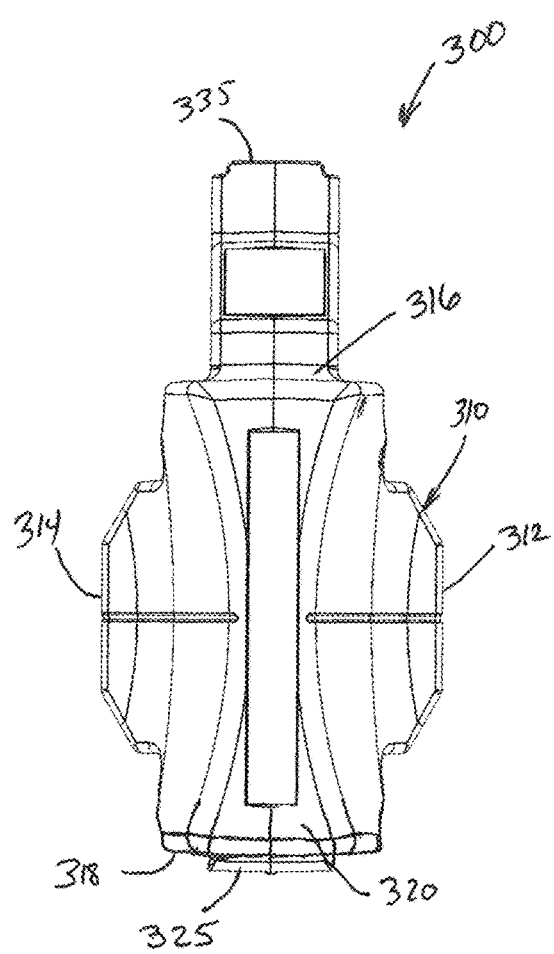
FIG. 30 is a top surface plan view of the medial antenna array of FIG. 25.
Figure 31:
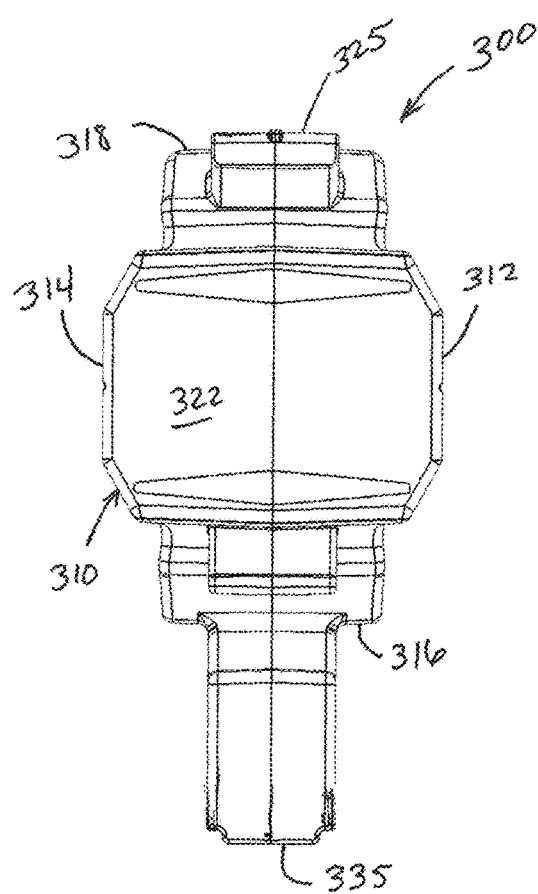
FIG. 31 is a bottom surface plan view of the medial antenna array of FIG. 25.

Referring to FIGS. 27 and 32, an electrical connector 360 provides power to the medial antenna array 300 and transmits the NMR signals detected by the antenna coils 350 to the MR scanner. An opening 355 is located within the lower horizontal portion of the connection arm 335. The electrical connector 360 is mounted within the opening 355 and generally orthogonal to the bottom surface 342 of the connection arm 335, such that the electrical connector 360 may engage a complementary electrical connector 420 on the junction box 400.

Figure 33:
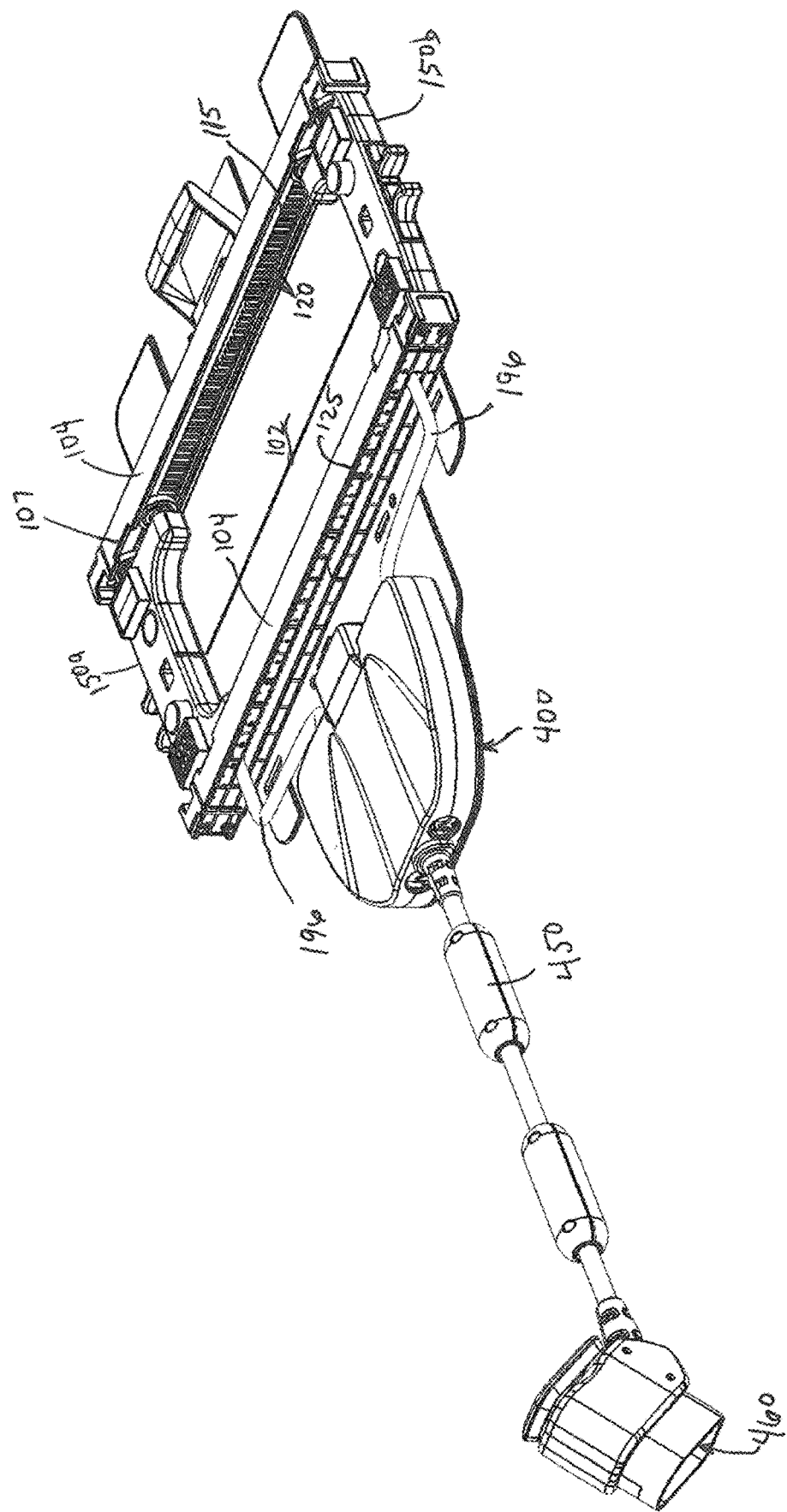
FIG. 33 is an isometric view of the antenna support structure, junction box, and scanner cable as shown in the MR support and imaging system of FIG. 1.

Turning next to FIG. 33, the antenna support structure 100 includes a base plate 102 which is generally planar and configured to be positioned on the surface supporting the MR imaging and patient support system 10. The lower side of the base plate 102 is set on the surface supporting the MR imaging and patient support system 10 and the upper side of the base plate 102 is configured to receive a pair of rails 104.

Figure 34:
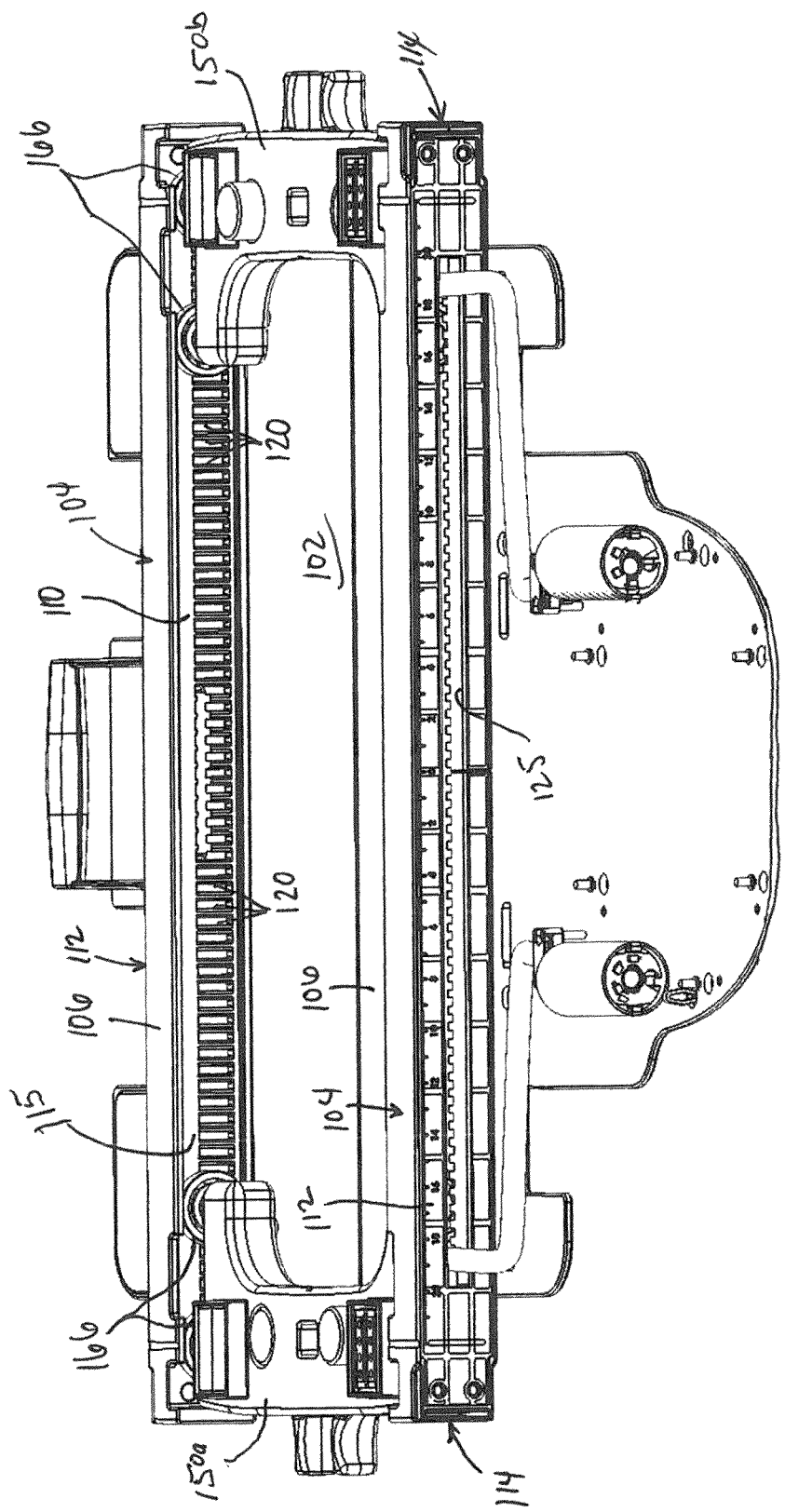
FIG. 34 is a view of the antenna support structure from the top and front of the antenna support structure as shown in FIG. 33.
Figure 37:
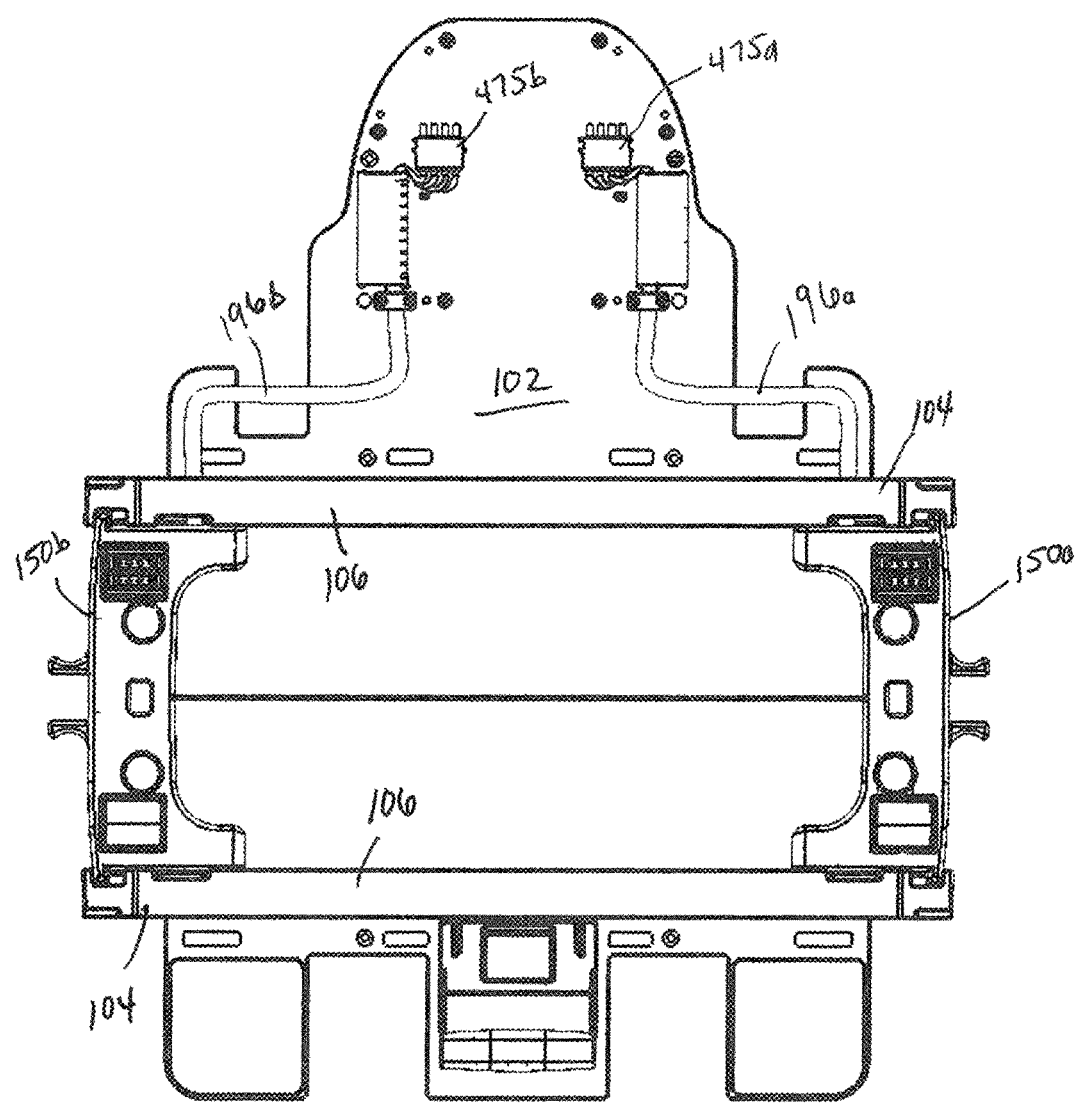
FIG. 37 is a top plan view of the antenna support structure as shown in FIG. 33.

The rails 104 are mounted parallel to each other and in an orientation that is transverse to the surface supporting the MR imaging and patient support system 10 and extend longitudinally between each side of the base plate 102. A first rail 104 is mounted proximate to the front edge of the base plate 102 and a second rail 104 is mounted proximate to the rear edge of the base plate 102. With reference also to FIGS. 34-36, each rail 104 is configured to receive one end of a carriage 150. Each rail 104 has a bottom surface 108 mounted to the base plate 102 and a top surface 106, opposite the bottom surface and distal from the base plate 102. Each rail 104 further includes an inside surface 110 configured to receive the carriage 150 and an outside surface 112 opposite the inside surface 110. The rails 104 are mounted to the base plate such that the inside surfaces 110 of each rail face each other and face toward a central axis of the base plate 102. The inside surface 110 is recessed inward toward the center of the rail 104 from an inside edge of the top surface 106 and an inside edge of the bottom surface 108.

The rails 104 provide a system for movably mounting the carriages 150 to the base plate 102. The inside surface 110 is recessed a sufficient distance such that wheels 166 mounted on the carriage 150 may ride in a channel 115 formed by the bottom side of the top surface 106, the inside surface 110, and top side of the bottom surface 108. The inside surface 110 further includes a series of slots 120 cut along the inside surface 110. Each slot 120 is configured to receive a complementary tab 181 extending from the carriage 150 and are configured to hold the carriage 150 in position with respect to the rail 104. A segment 119 of the inside surface 110 adjacent each end 114 of the rail has no slots 120 and provides a home position for the carriage 150. As will be discussed in more detail below, the lateral antenna arrays 200 may be connected and disconnected at the home position. The slots 120 are then consecutively spaced along the inside surface 110 between each of the end segments 119. A positioning guide is included along the outside surface 112 of each rail. The positioning guide includes a plurality of indices 122 spaced apart along the outside surface 112. According to the illustrated embodiment the indices 122 include a series of vertical lines and numbers identifying a position along the series of vertical lines. Optionally, other symbols and/or letters may be used as indices 122. A positioning tab 211 located at the bottom on each side 216, 218 of the lateral antenna array 200 (see FIGS. 15-23) ends at the bottom surface 222 of the lateral antenna array 200 and is adjacent to the top surface 106 of the rail when the array 200 is mounted to the carriage 150. The positioning tab 211 aligns with at least one index 122 during imaging to identify the location of the lateral antenna array 200 along the rails 104.

At least one rail 104 includes a slot 125 extending through the rail 104. The slot 125 passes between the inside surface 110 and the outside surface 112 and extends longitudinally along the rail 104. Each end of the slot 125 is displaced centrally inward along the rail 104 from the end 114 of the rail 104. The slot 125 has a height sufficient to receive a cable 196 from the carriage 150. The cable 196 passes through the slot 125 and moves along the slot 125 as the carriage 150 moves along the rail, allowing each carriage 150 to be electrically connected to the junction box 400 positioned outside of the rails 104.

With reference to FIGS. 39-44, a carriage 150 according to one embodiment of the invention is illustrated. The carriage 150 illustrated in these figures is the left carriage 150b. The term left is relative with respect to the orientation from which the MR imaging and patient support system 10 is being viewed and is not intended to be limiting. Similar to the lateral antenna arrays 200, which are mounted to the carriages 150, the right and left lateral carriages 150a, 150b have substantially identical construction with some elements mirrored about a central axis of the carriage such that the right and left carriages 150a, 150b may be mounted on opposite sides of the antenna support structure 100. For convenience, only the left carriage 150b will be described in detail herein. However, the description is generally applicable to the right carriage 150a as well.

Each carriage 150 includes a housing 151 substantially enclosing the components within the carriage 150. The housing 151 includes a bottom surface 162 positioned proximate to but spaced apart from the base plate 102 when the carriage 150 is mounted on the rails 104 and an top surface 160 opposite the bottom surface 162 and distal from the base plate 102 when the carriage 150 is mounted on the rails 104. The housing 151 also includes a front surface 156 and a rear surface 158, opposite the front surface 156. Each of the front and rear surfaces 156, 158 include cylindrical hubs 164 protruding from the respective surface. The cylindrical hubs 164 receive wheels 166 mounted thereto, where the wheels 166 ride in the channel 115 along the inside of each rail 104. The housing 151 also includes an inner surface 152 configured to face away from the center of the antenna support structure 100 when the carriage 150 is mounted on the rails 104. The inner surface 152 includes a pair of outer segments, each outer segment proximate to either the front surface 156 or the rear surface 158. The outer segment of the inner surface 152 extends inward and generally orthogonally from the front and rear surface 156, 158 for a distance. The inner surface 152 then includes a curved segment between the pair of outer segments. The curved surface has a concave curvature inward to the carriage 150. The inner surface 152 is configured to align generally to the inner surface 212 of the lateral antenna array 200. The housing 151 further includes an outer surface 154 configured to face away from the center of the antenna support structure 100 when the carriage 150 is mounted on the rails 104. The outer surface 154 includes an opening 168 configured through which actuators for a slide mechanism 175 extend.

Figure 45:
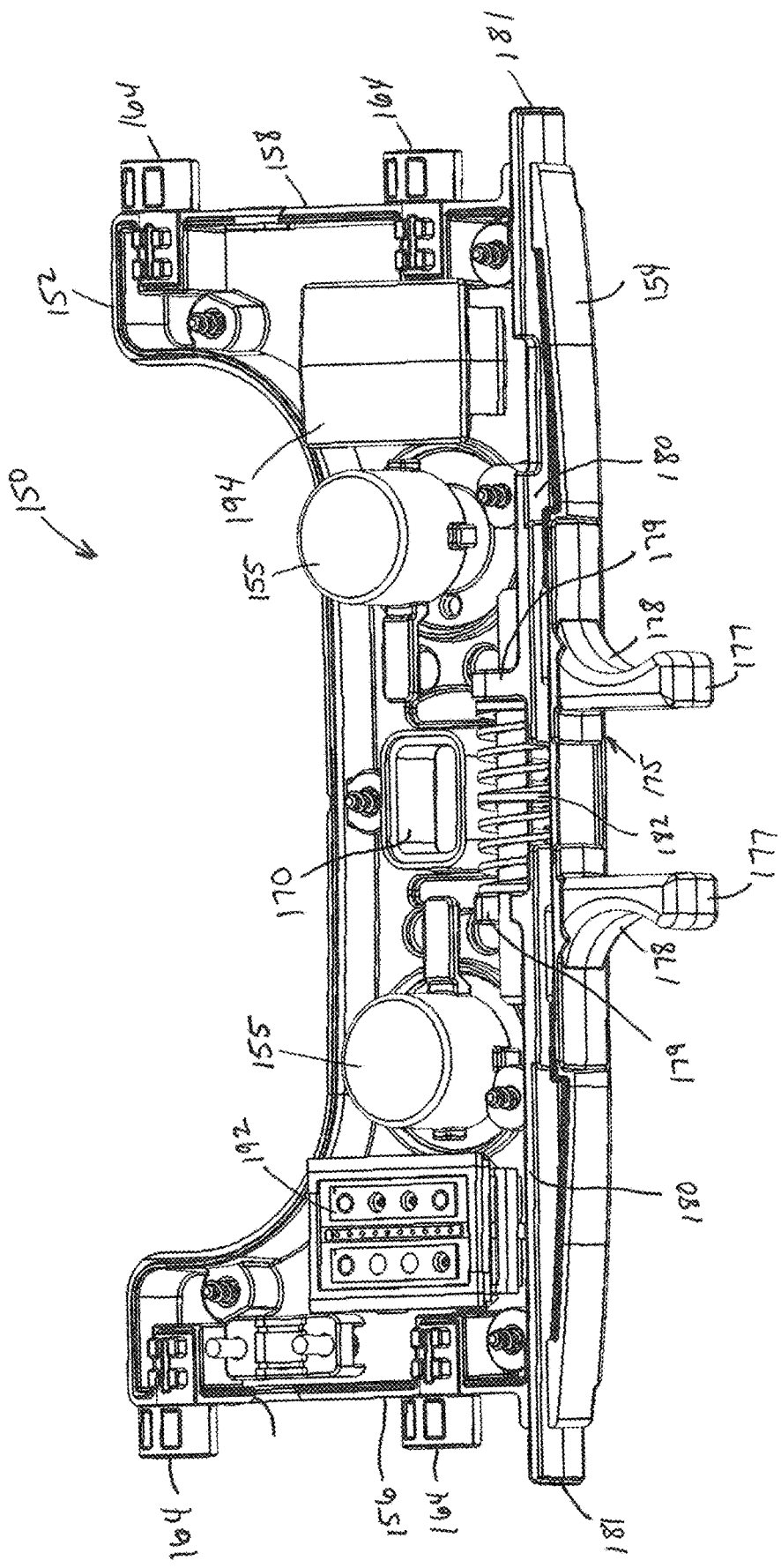
FIG. 45 is a view of the carriage for the antenna support structure as shown in FIG. 39 from the top and the side with the top cover removed.

The slide mechanism 175 is used to retain the carriage 150 at one of the positions identified by the indices 122 on the positioning guide along the rails 104. With reference also to FIG. 45, the slide mechanism 175 includes a pair of actuators 177 where each actuator 177 includes an external portion 178 and an internal portion 179. The external portion 178 protrudes through the opening 168 in the carriage housing 151 and is configured to be manually actuated, for example, by pressing the external portions 178 together. The internal portion 179 of each actuator 177 is connected to a slide 180 that extends longitudinally form the actuator out one end of the carriage 150. The internal portion 179 also extends into the carriage beyond the slide 180 and is used to compress a spring 182 within the carriage 150. The spring 182 normally biases the actuators 177 apart and the slides 180 to an extended position. When the slides 180 are extended a tab 181, or end of each slide 180, extends outward through a slot defined between either the front surface 156 or rear surface 158 and the outer surface 154 of the carriage 150. The tab 181 is configured to engage one of the slots 120 in the rail 104 to retain the carriage 150 in position with respect to the rails 104. When the actuators 177 are pressed together, the internal portions 179 of each actuator compress the spring 182 and move the slides 180 to a retracted position. When the slides 180 are in a retracted position, the tabs 181 on each slide are moved within the carriage 150 and disengage from the slots 120 in the rail 104, allowing the carriage 150 to be moved laterally along the rails 140. When the actuators 177 are released, the spring 182 again biases the actuators 177 and slides 180 outward, returning them to the extended position.

An electrical connector 192 extends, at least in part beyond the top surface 160 of the carriage 150. The electrical connector 192 is complementary to, the electrical connector 240 positioned on the bottom surface 222 of the lateral antenna array 200, delivering power to the array 200 and transmitting the NMR signals detected by the antenna coils 250 to the MR scanner. A pair of openings 190 is formed in the top surface 160 of the carriage to receive the electrical connector 192. As previously indicated, at least a portion of the components within the carriage 150 may be located within the array in a position that is mirrored about a central axis of the carriage 150 depending on whether it is a right carriage 150a or a left carriage 150b. Thus, a first opening 190 is located proximate the front surface 156 of the carriage 150, and a second opening 190 is located proximate the rear surface 158 of the carriage 150. An electrical cable 196 has a first end and a second end and the first end is connected to the electrical connector 192 within the carriage 150. The cable 196 then extends out of the carriage 150, through the slot in the rail 104 and to the junction box 400. The second end of the cable 196 is terminated in the junction box 400 and establishes an electrical connection to a seamier cable 450.

Although the same housing 151 is used for each of the right and left carriages 150a, 150b the connector 192 extends through the opening 190 located toward the front surface 156 of the respective carriage 150 in a manner similar to that discussed above with respect to the lateral antenna arrays 200. When a carriage 150 is mounted to the left side of the antenna support structure 100 and is designated as the left carriage 150b the front and rear surfaces correspond to the front and rear surfaces 156, 158 as illustrated in FIGS. 39-45 and as discussed above. When a carriage 150 is mounted to the right side of the antenna support structure 100 and is designated as the right carriage 150a, the carriage is rotated about the central axis with respect to the left carriage 150b such that the inner surface 152 remains directed toward the center of the antenna support structure 100. As a result of the rotation, the front and rear surfaces of the left carriage 150b become the rear and front surfaces, respectively, of the right carriage 150a. The connector 192 is positioned within the opening 190 proximate to the front surface 156 of the carriage 150 and a cover 194 is placed over the opening 190 proximate to the rear surface 158 of the carriage 150.

Each carriage 150 also includes a pair of ejectors 155, where each ejector 155 extends through an opening 153 in the top surface 160 of the carriage 150. Each ejector 155 is biased outward by a spring. When a lateral antenna array 200 is mounted to the carriage 150, the bottom surface 222 of the lateral antenna array 200 engages the ejectors 155 and compresses the springs. The springs have sufficient force to overcome the friction force between the electrical connectors 192, 240 of the carriage 150 and the lateral antenna array 200, respectively. As a result, the ejectors 155 can push the lateral antenna array 200 away from the carriage 150 if no opposing force is applied to retain the lateral antenna array 200 to the carriage 150.

Figure 38:
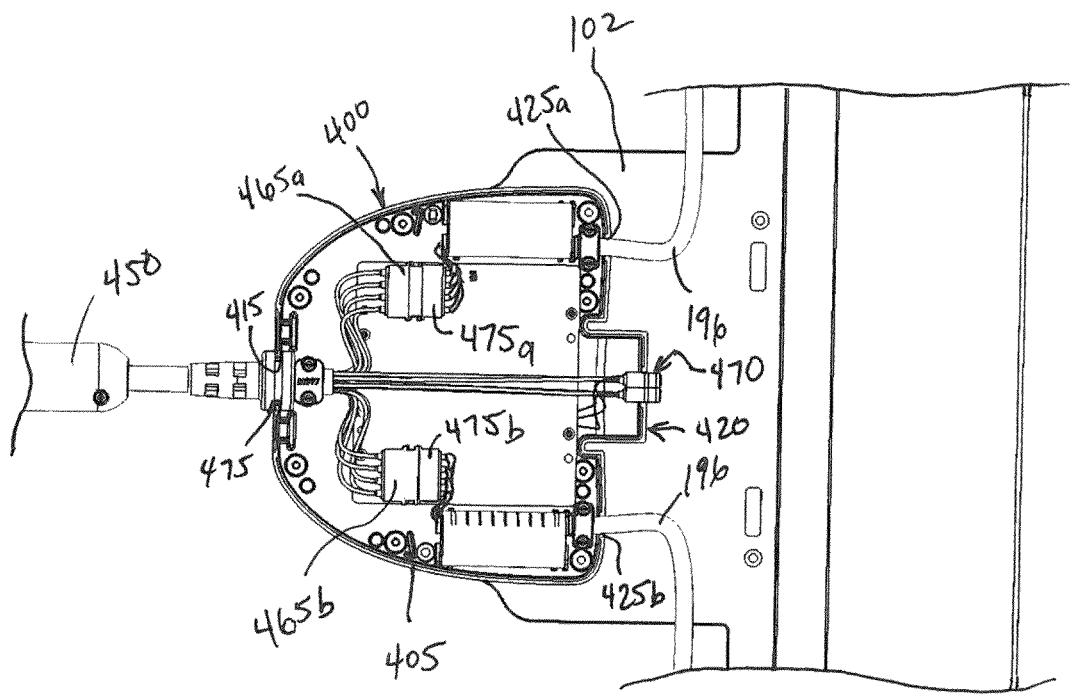
FIG. 38 is a partial top plan view of the antenna support structure as shown in FIG. 33 with the top cover of the junction box removed.
Figure 39:
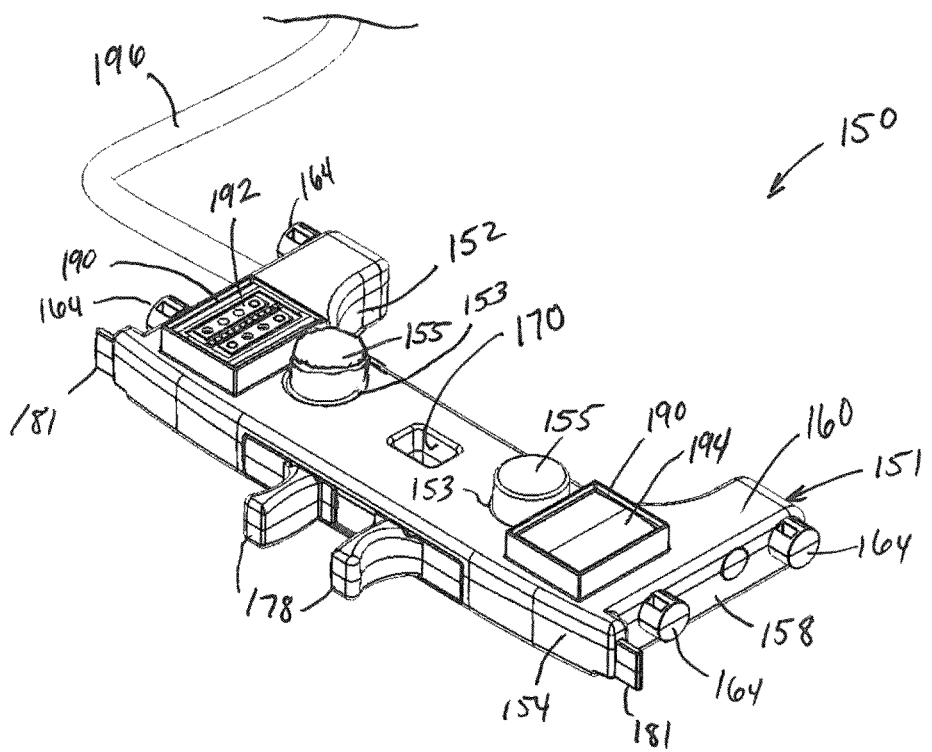
FIG. 39 is an isometric view of a carriage for the antenna support structure as shown in FIG. 33.
Figure 40:
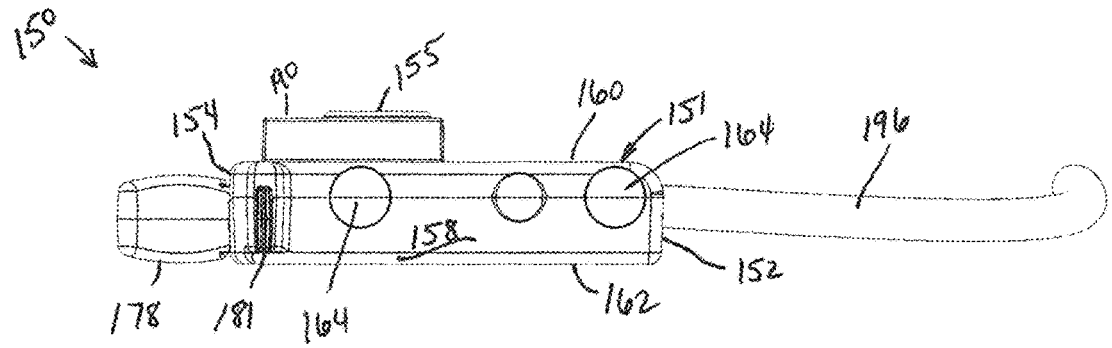
FIG. 40 is a rear elevation view of the carriage for the antenna support structure as shown in FIG. 39.
Figure 41:
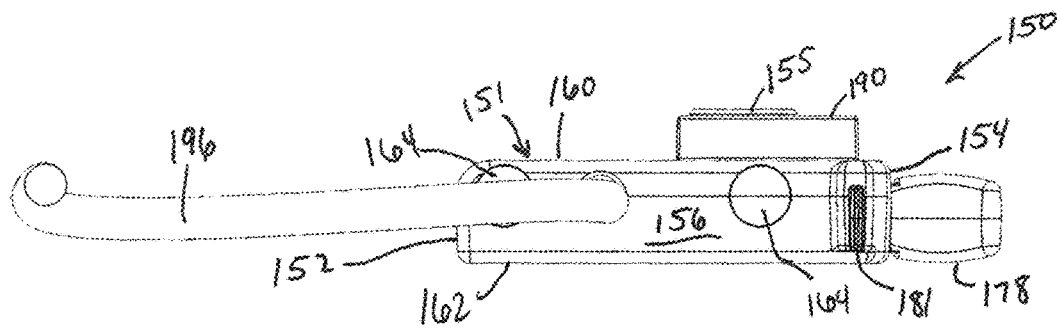
FIG. 41 is a front elevation view of the carriage for the antenna support structure as shown in FIG. 39.
Figure 42:
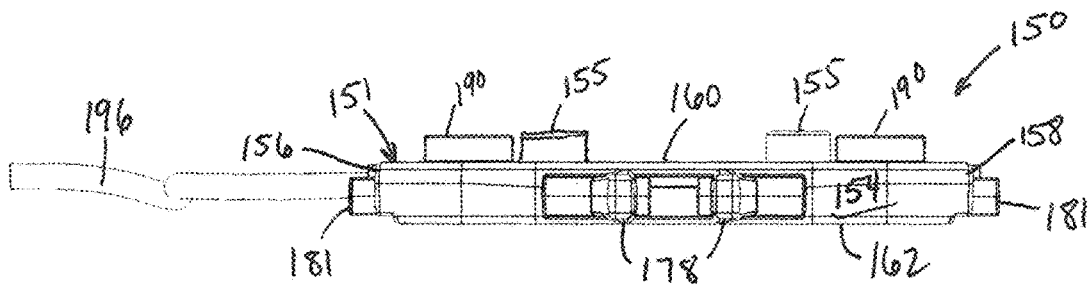
FIG. 42 is a first, side elevation view of the carriage for the antenna support structure as shown in FIG. 39.
Figure 43:
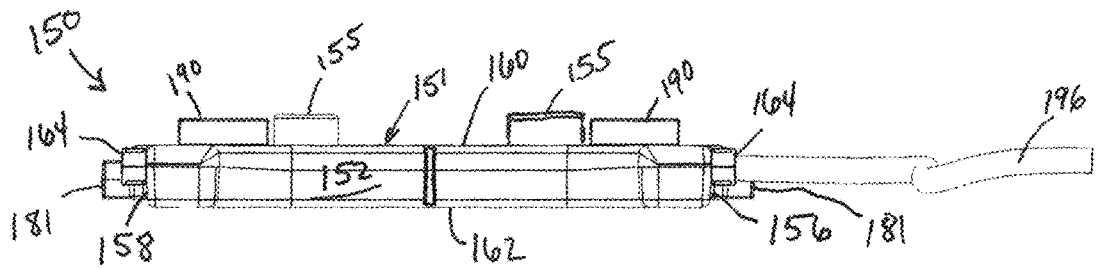
FIG. 43 is a second side elevation view of the carriage for the antenna support structure as shown in FIG. 39.
Figure 44:
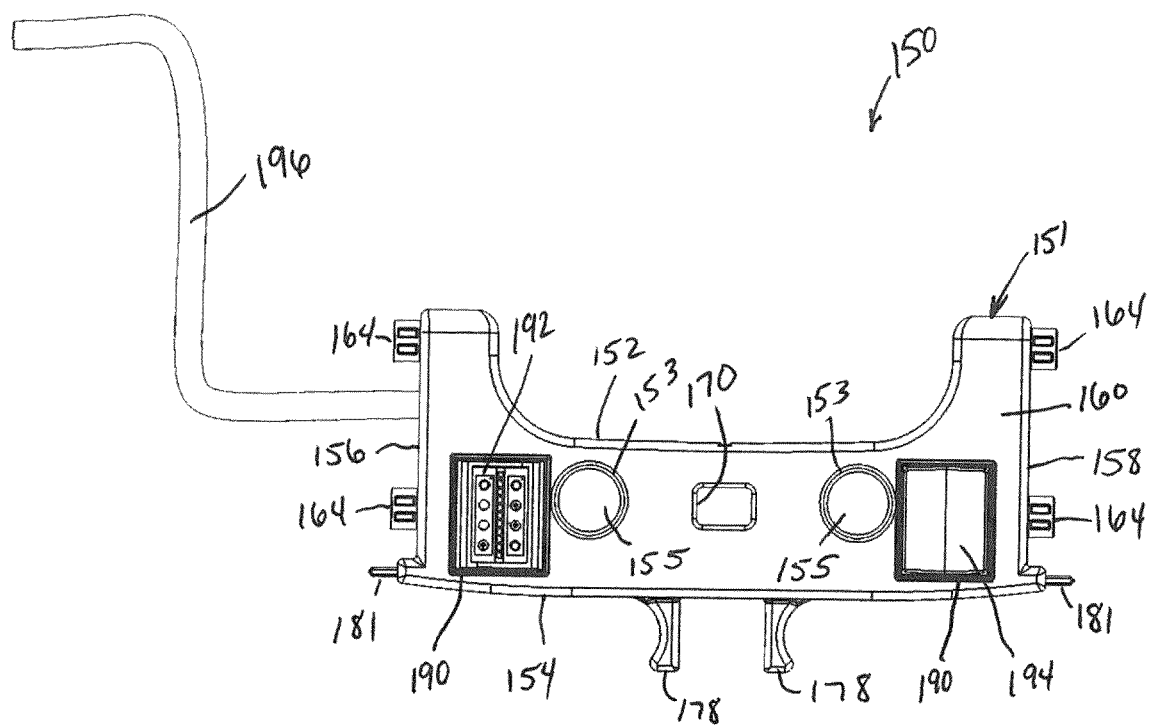
FIG. 44 is a top plan view of the carriage for the antenna support structure as shown in FIG. 39.

Turning next to FIGS. 13-14 and 38, the MR imaging and patient support system 10 includes a junction box 400 configured to establish electrical connections between each of the antenna arrays 200, 300 and a scanner cable 450. The junction box 400 has a lower housing 405 and an upper housing 410. The two halves of the junction box 400 are removable mounted to each other to provide access to electrical connections made within the junction box 400. An opening 415 is located at the front end of the junction box 400 and is configured to receive a scanner cable 450. The opening 415 is preferably formed in part in the lower housing 405 and in part in the upper housing 410. The junction box 400 also includes a medial antenna array connector 420 on the rear of the junction box 400 configured to engage the electrical connector 360 from the medial antenna array 300, and openings 425 configured to receive the cables 196 from each carriage 150.

The scanner cable 450 may be provided by the manufacturer of the MR scanner and includes a plug 460 at a first end of the cable 450 connectable to the MR scanner. The second end of the scanner cable 450 provides for an interconnection to the antenna arrays. The cable includes a strain relief member 475 on the cable where the strain relief member 475 connects to the at least one of the lower housing 405 and the upper housing 410 such that the forces applied to the scanner cable 450 external to the junction box 400 are translated to the junction box 400 rather than to a connector. According to the illustrated embodiment, the strain relief member 475 includes a channel formed within the member and around the periphery of the cable 450. The channel slides on to the wall of the lower housing 405 and receives the wall of the upper housing 410 when the upper housing 410 is connected to the lower housing 405. According to the illustrated embodiment, the scanner cable 450 includes a bundle of conductors, where each conductor transmits a signal corresponding to one of the antenna coils 250, 350 in either the lateral antenna array 200 or the medial antenna array 300 from the respective antenna coil 250, 350 to the MR scanner. The cable 450 is terminated at the second end with a set of three electrical connectors. Two of the electrical connectors are lateral array connectors 465 and the third electrical connector is a medial array connector 470. Each lateral array connector 465 is connected to a complementary electrical connector 475 provided within the junction box. Each of the complementary electrical connectors 475 has conductors extending from the connector 475 to a balun 480 and, in turn, to conductors within the cable 196 from each carriage. The medial array connector 470 is connected directly to and forms, in part, the medial antenna connector 420 on the junction box 400.

In operation, the MR imaging and patient, support system 10 supports a patient on an imaging table and allows for adjustment of the antenna arrays 200, 300 independent of the support structures 20, 40. Each of the first and second patient support structures 20, 40 as well as the antenna support structure 100 may be initially placed on the imaging table in preparation to receive a patient. Additional pads may be provided for further patient comfort and support if required. In the embodiment illustrated in FIG. 1, a first additional pad 12 is provided behind the first support structure 20. The first additional pad 12 is wedge shaped to provide additional support for the patient in the transition from the imaging table to the first patient support structure 20. A second additional pad 13 may be located over the junction, box and provides support for a patient's arms during imaging. The second additional pad 13 may include hand grips 15 molded into the pad to provide an indication of where the patient should place their hands during imaging.

The antenna support structure 100 is first configured according to the imaging procedure to be performed. According to the embodiment illustrated in FIG. 1, the antenna support structure 100 is configured to image both breasts in tandem. The medial antenna array 300 may be connected to the base plate 102 by positioning the c-shaped hook 325 around the rear rail 104 and pivoting the medial antenna array forward such that the bottom surface 322 rests on the base plate 102 and the front rail is positioned between the front edge 331 of the boss 330 and the rear surface 341 of the connection arm 335. The lower horizontal surface of the hook 325 engages the rear rail 104 to help align the medial antenna array 300 laterally with respect to the rails 104.

Figure 46:
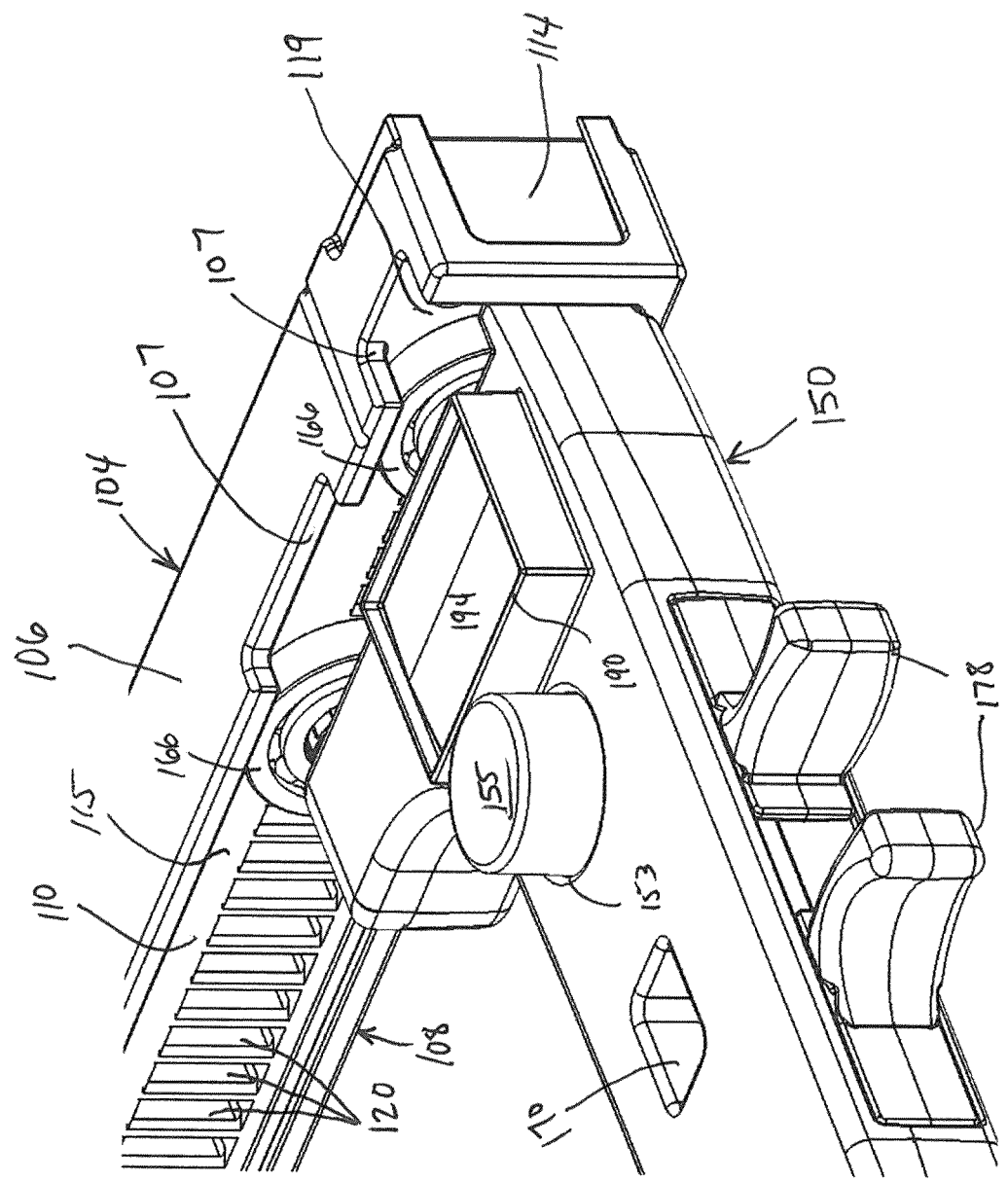
FIG. 46 is a partial isometric view illustrating a home position of a carriage with respect to a rail from the antenna support structure as shown in FIG. 39.

Each lateral antenna array 200 is then mounted to one of the carriages 150. The actuators 177 on the slide mechanism 175 are pressed together, causing each tab 181 to be retracted from the slots 120 on the rails 104 and allowing the carriages 150 to be moved. The carriages 150 are each moved to the end 114 of the rail, which will be referred to as a "home" position. At the home position, the inside surface 110 of the rail 104 does not have any slots 120 such that when the actuators 177 are released, the tabs 181 cannot extend fully and the carriage 150 is not positively retained at the home position. Referring to FIG. 46, the top surface 106 of each rail includes a pair of cutouts 107 along the inside edge of the top surface 106 and proximate the home position. One of the cutouts 107 is configured to receive the first tab 226 and the other of the cutouts 107 is configured to receive the second tab 228 from the bottom of the lateral antenna array 200. As the lateral antenna array 200 is pressed onto the carriage 150, the electrical connectors 240, 192 of the lateral antenna array and the carriage 150 engage, establishing an electrical connection therebetween; the bottom surface 222 of the lateral antenna array 200 compresses the ejectors 155; and the tabs 226, 228 fit through the cutouts 107 on the rail 104. Because the tabs 181 on the slide mechanism 175 are not inserted into a slot on the rail 104, the carriage 150 and lateral antenna array 200 may be slid forward while pressing down on the antenna array 200. As the carriage moves forward, the tabs 226, 228 on the bottom of the lateral antenna array 200 engage the bottom side of the top surface 106 of each rail 104, presenting an opposing force sufficient to overcome the ejectors 150 and retaining the lateral antenna array 200 to the carriage 150. If a different configuration is desired, the carriage 150 is again returned to the home position and the ejectors 150 separate the lateral antenna array 200 from the carriage 150 by separating the electrical connectors 192, 240 and pushing the tabs 226, 228 on the lateral antenna array 200 through the cutouts 107 on the rail 104.

Figure 50:
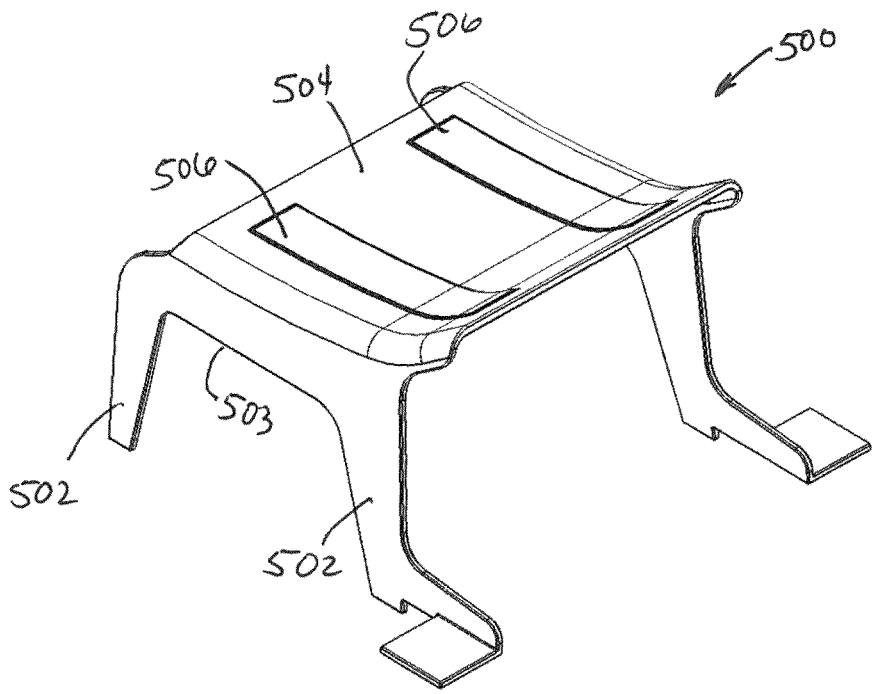
FIG. 50 is an isometric view of a breast support structure for use with the MR support and imaging system of FIG. 1.
Figure 51:
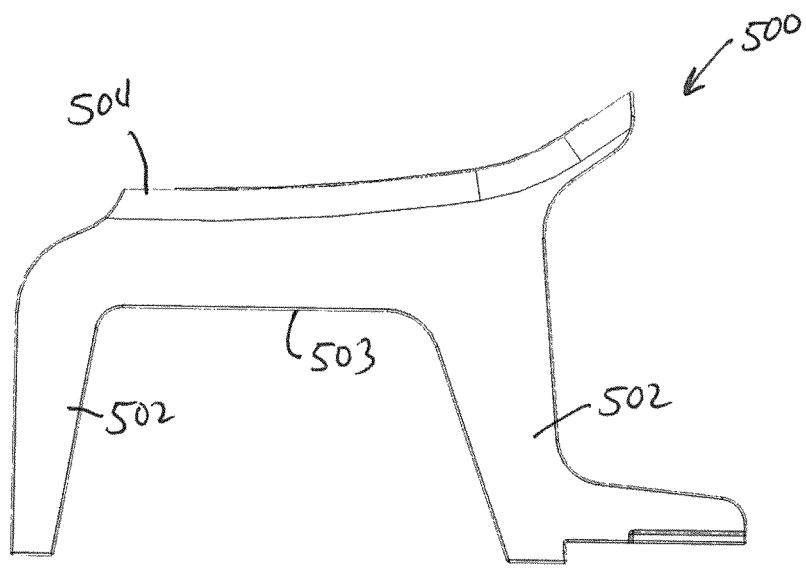
FIG. 51 is a side elevation view of the breast support structure of FIG. 50.
Figure 52:
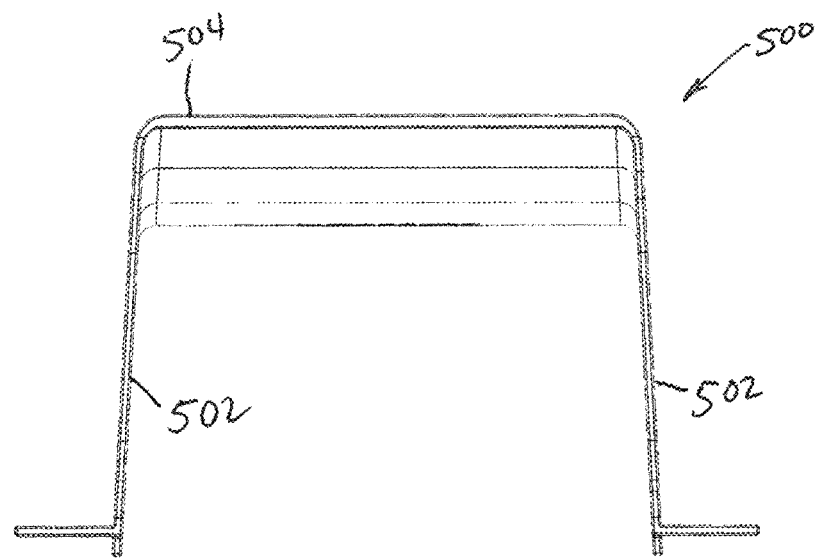
FIG. 52 is a rear elevation view of the breast support structure of FIG. 50.
Figure 53:
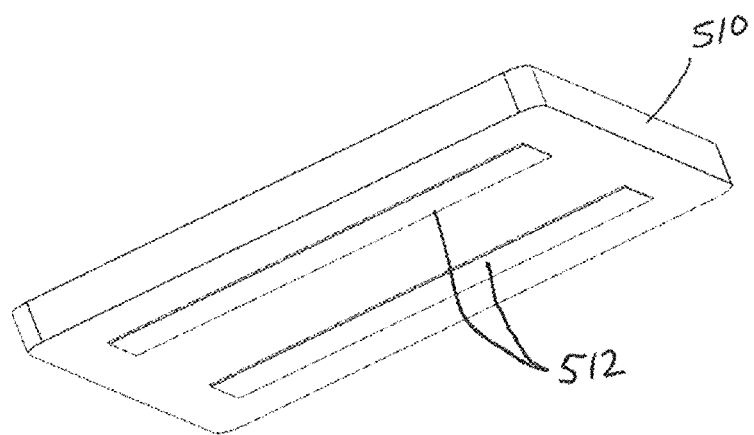
FIG. 53 is an isometric view of a breast pad for use with the breast support structure of FIG. 50.

As previously discussed, it is contemplated that the antenna support structure 100 may be configured for different imaging applications. The medial antenna array 300 may be used with a single lateral antenna array 200 or two lateral antenna arrays 200 may be used without the medial antenna array 300 to image a single breast. When a single breast is being imaged, the second breast may be suspended downward next to the antenna arrays 200, 300 performing the imaging, or a breast support structure 500 may be positioned under the second breast not being imaged to keep the second breast clear of the procedure. With reference to FIGS. 50-52 an exemplary breast support structure 500 is illustrated. The illustrated breast support structure 500 includes legs 502 on each corner of the structure 500 and an upper surface 504 spanning between each of the legs 502. An opening 503 is present between the legs 502 and an open chamber exists under the breast support structure 500. According to another embodiment of the invention, a wall (not shown may extend along a front and rear sides of the breast support structure 500 rather than separate legs 502. The opening 503 may span between the walls and the open chamber still exists under the breast support structure 500. The upper surface 504 may include one or more attachment strips 506 configured to engage a breast support pad 510 as shown in FIG. 53. Each of the attachment strips 506 may be of any suitable material to retain the breast support pad 510 in position on the upper surface 504. For example, the attachment strip 506 may be one half of a hook and loop fastening system, and the other half of the hook and loop fastening system is secured to the bottom of the breast support pad 510. Optionally each attachment strip 506 may be made of a soft plastic or rubber to provide a high sliding friction surface to retain the breast support pad 510 in place.

Figure 47:
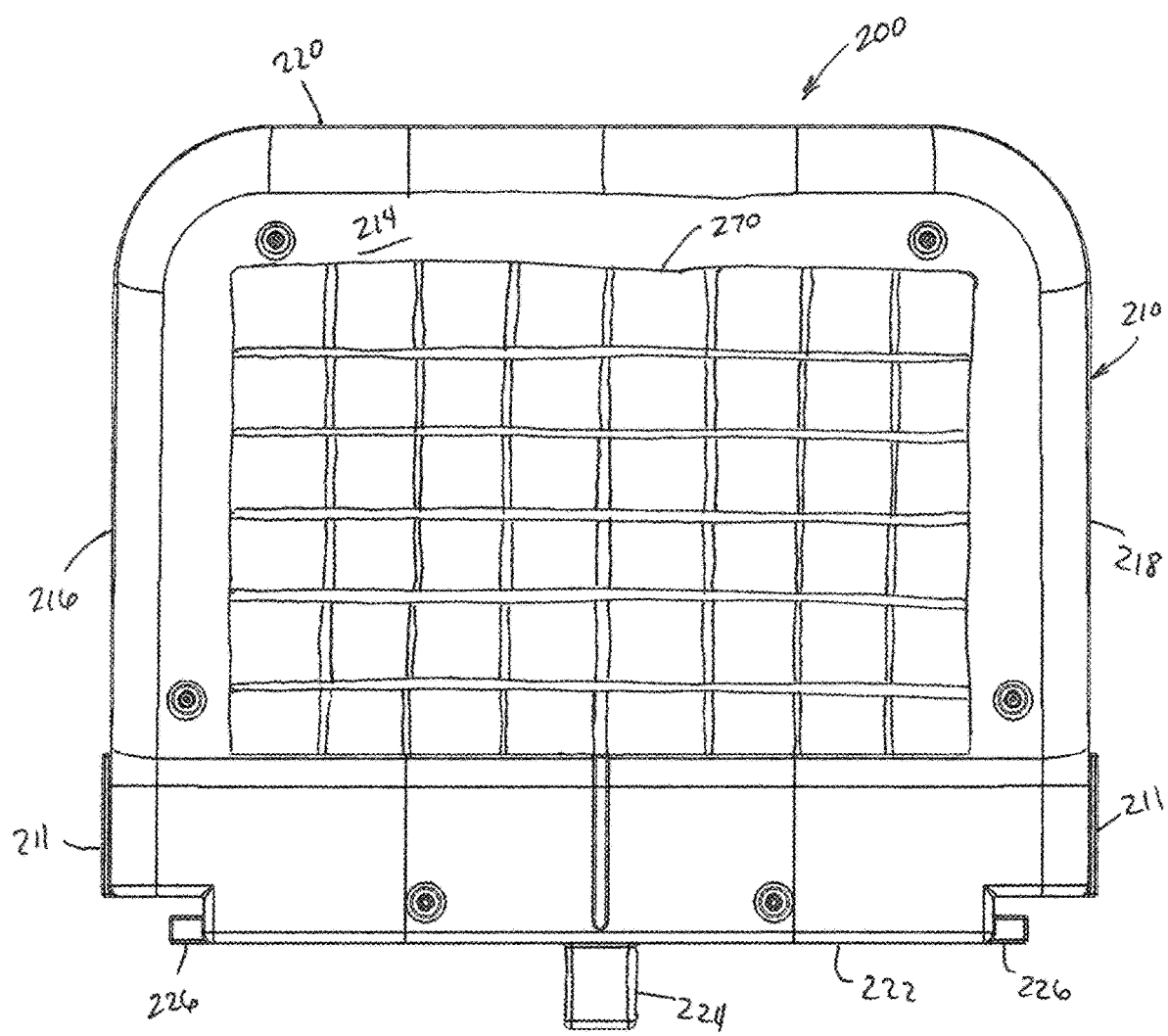
FIG. 47 is an outer surface elevation view of a left lateral antenna array including a biopsy grid according to another aspect of the invention.
Figure 49:
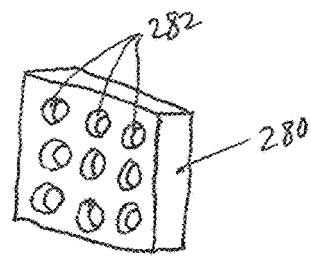
FIG. 49 is a grid block insertable into the biopsy grid of FIG. 47 and FIG. 48.
Figure 48:
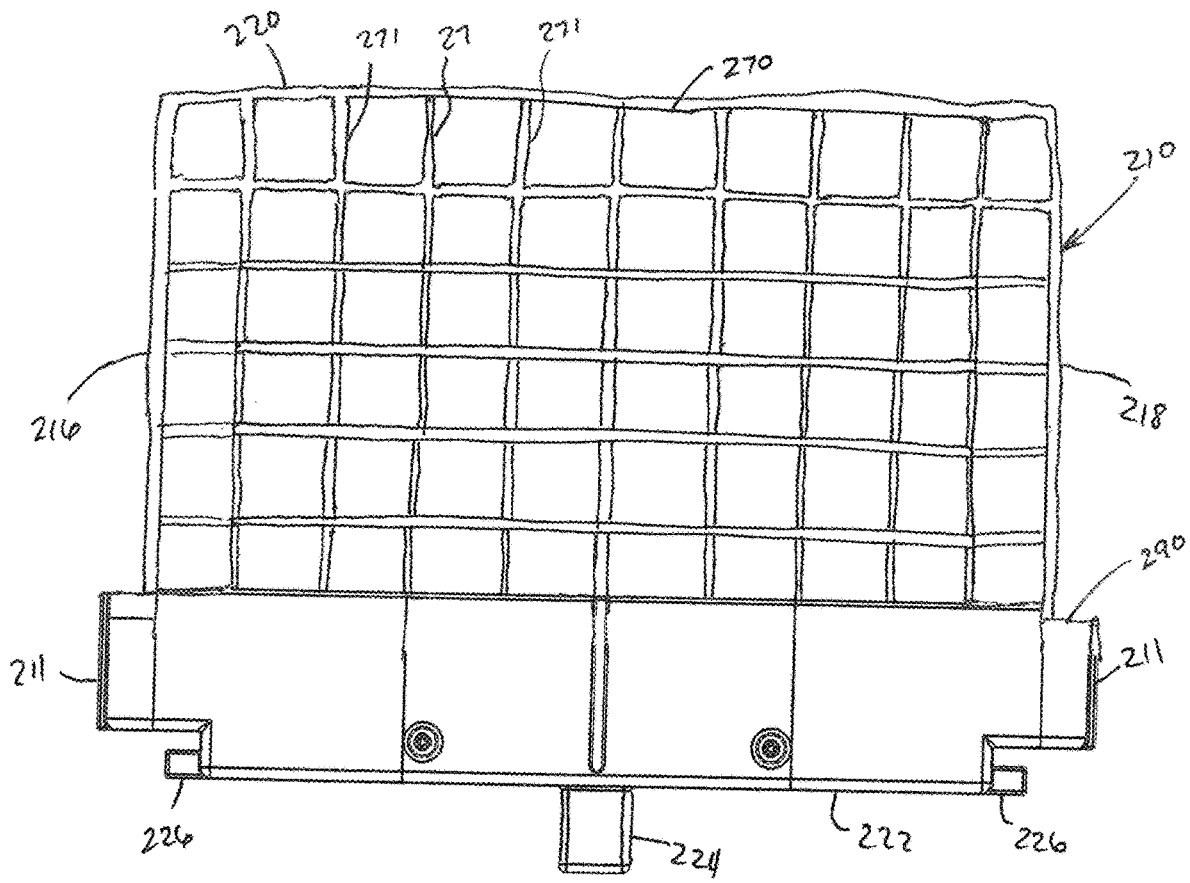
FIG. 48 is an outer surface elevation view of a biopsy grid mountable to a carriage according to another aspect of the invention.
Figure 54:
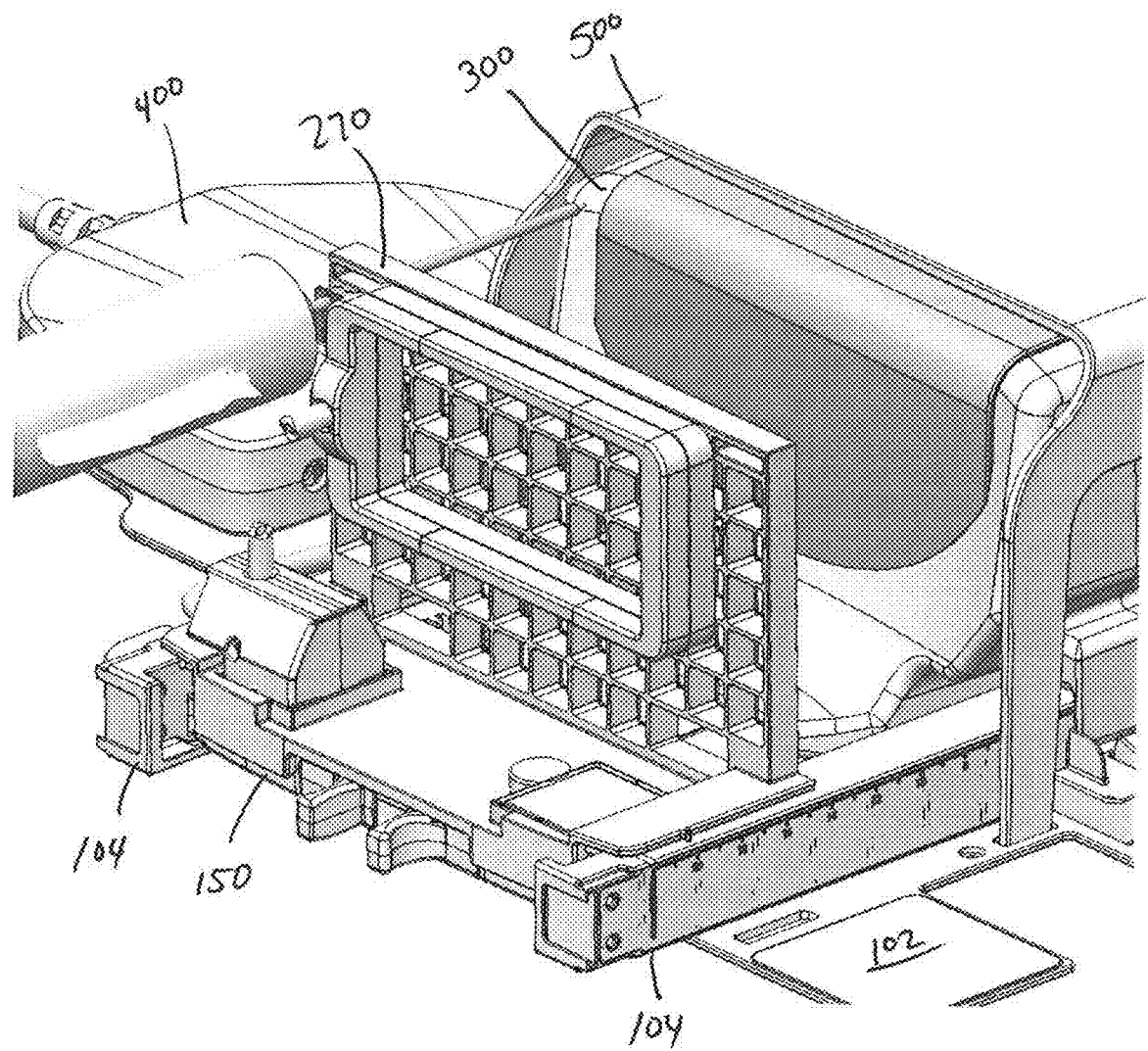
FIG. 54 is a partial isometric view of the breast support structure of FIG. 50 in use with biopsy grid and the MR support and imaging system according to an exemplary application of the present invention.

The breast support structure 500 may be used, for example, when a biopsy is conducted during MR imaging. When performing a biopsy, the lateral antenna array 200 may include, for example, a biopsy grid 270 within the central region of the antenna array 200, as shown in FIG. 47. The biopsy grid 260 may be used with a medial antenna array 300 as shown FIG. 54, or with a lateral antenna array 200 depending on the location of the breast tissue to be biopsied. According to one embodiment of the invention, the lateral antenna array 200 may include a biopsy grid 270 and a single antenna coil 250 extending around the periphery of the housing as shown in FIG. 47. Optionally, a biopsy grid 270 may be used without an antenna coil 250 and may be mounted, to a chassis 290 configured to mount to the carriage 150 in the same manner as described herein with respect to the lateral antenna array 200. The biopsy grid 270 includes a plurality of openings 271 to assist in locating a biopsy needle. Referring also to FIG. 49, a biopsy block 280 may be provided which is insertable into individual openings 271 and which, in turn, includes multiple apertures 282 sized to receive a biopsy needle. The breast support structure 500 is located under the breast not undergoing the biopsy to raise the breast tissue above the biopsy grid and keep the area underneath the breast support structure open for a health care professional to access to perform the biopsy as necessary.

After the antenna support structure 100 is configured for the imaging procedure to be performed, the patient is positioned on the support structures 20, 40 and between the antenna arrays 200, 300. As the patient is positioned on the imaging table, each of the first and second patient support structures 20, 40 as well as the antenna support structure 100 may be moved independently of the other to engage the patient's anatomy in a manner to provide improved support and comfort for the patient during imaging. One or both of the patient support pads 22, 24 may be included on the first patient support structure 20 depending on the size of the patient to help position the patient for imaging. The breast tissue to be imaged is positioned with respect to one of the antenna arrays 200, 300. Preferably, the breasts are initially positioned with respect to a stationary antenna array, such as the medial antenna array 300. A movable array, such as the lateral antenna array 200 is then positioned with respect to the breast tissue for imaging. The lateral antenna array 200 may be slid towards the medial antenna array 300 until the breast tissue is compressed between the medial and lateral arrays such that the breast tissue will not move during imaging. When imaging is complete, the lateral antenna array 200 may be moved away from the breast tissue as the patient gets up from the table.

During imaging, the patient's forehead and sides of the face rest on the head pad 41. The patient looks downward through the head pad 41 and, if present, the mirror assembly 80 as shown in FIG. 10 is positioned such that the patient may see out between the adjustable legs 60 of the second patient support structure 40. The mirror assembly 80 may help prevent claustrophobic feelings in the patient and allow the patient to see and better communicate with a health care professional performing the scan. Because MR images can be lengthy, a video screen may be placed proximate the second support structure 40 and in line with the mirror assembly 80 allowing the patient to view entertainment during the procedure.

It should be understood that the invention is not, limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A modular patient and antenna support system configured to move with respect to a surface on which it is located during medical imaging, the system comprising:
   a first patient support structure including a lower support member and an upper support member, wherein:

the lower support member is configured to be placed on a scan table during medical imaging, the upper support member is mounted to the lower support member and is configured to engage an abdominal region of a patient, and the lower support member is configured to move on the scan table to position the first patient support structure with respect to the patient;

a second patient support structure including a base and a head rest, wherein:

the base is configured to be placed on the scan table during medical imaging, the head reset is mounted to the base and is configured to engage and support a head of the patient, the base is configured to move on the scan table to position the second patient support structure with respect to the patient, and the second patient support structure is configured to move independent of the first patient support structure;

an antenna support structure including:

a base plate;

a plurality of antenna arrays, wherein each antenna array includes:

a housing having a first mounting surface, and at least one antenna coil located within the housing; and at least one carriage movably mounted to the base plate, wherein:

the at least one carriage includes a second mounting surface, the first mounting surface of a first antenna array, selected from the plurality of antenna arrays, is removably mounted to the second mounting surface of a first carriage, the first carriage selected from the at least one carriage, the first carriage is configured to move with respect to the base plate, and the first carriage positions the first antenna array with respect to the patient when the first antenna array is mounted to the first carriage, the base plate is configured to move on the scan table, and the antenna support structure is configured to be positioned between the first patient support structure and the second patient support structure and is configured to move independent of the first and the second patient support structures.

2. The modular patient and antenna support system of claim 1, wherein each of the plurality of antenna arrays is removably mounted to one of the base plate and the at least one carriage.

3. The modular patient and antenna support system of claim 2, wherein:

a second antenna array, selected from the plurality of antenna arrays, is fixed with respect to the base plate when mounted to the base plate, and the first antenna array is moved along the base plate via the first carriage to position an anatomy of the patient to be imaged between the first antenna array and the second antenna array.

4. The modular patient and antenna support system of claim 3, wherein the second antenna array includes a support surface distal from the base plate, the support surface engaging a third anatomical region of the patient to, at least in part, support the patient.

5. The modular patient and antenna support system of claim 3, wherein:

the anatomy of the patient to be imaged is a first breast and a second breast;

the at least one carriage on which the first antenna array is mounted is a first carriage;

the first mounting surface of a third antenna array, selected from the plurality of antenna arrays, is removably mounted to the second mounting surface of a second carriage, the second carriage is selected from the at least one carriage, the second carriage is configured to move with respect to the base plate, the second carriage positions the second antenna array with respect to the patient when the second antenna array is mounted to the second carriage, the first and third antenna arrays are positioned on opposite sides of the second antenna array, the first antenna array is moved along the base plate via the first carriage to position the first breast between the first antenna array and the second antenna array, and the third antenna array is moved along the base plate via the second carriage to position the second breast between the third antenna array and the second antenna array such that the first and second breasts may be imaged in tandem.

6. The modular patient and antenna support system of claim 2, wherein:

the at least one carriage on which the first antenna array is mounted is the first carriage;

an anatomy of the patient to be imaged is one breast of the patient;

a second antenna array, selected from the plurality of antenna arrays, is mounted to a second carriage and is movable with respect to the base plate when mounted to the second carriage, and the first and second antenna arrays are moved along the base plate via the corresponding first and second carriage to position the breast of the patient for imaging between the first antenna array and the second antenna array.

7. The modular patient and antenna support system of claim 6, wherein one of the first and the second antenna arrays includes a biopsy grid.

8. The modular patient and antenna support system of claim 1, further comprising:

at least one rail mounted to the base plate and the at least one carriage is movably connected to the at least one rail.

9. An antenna support structure for use with a first patient support structure and a second patient support structure during medical imaging of one or both breasts of a patient, wherein the antenna support structure, the first patient support structure, and the second patient support structure are each configured to be positioned on a scan table during the medical imaging, the antenna support structure comprising:

a base plate configured to be moved with respect to the scan table on which it is located during the medical imaging;

at least one rail mounted to the base plate;

at least one carriage movably mounted to the at least one rail, the at least one carriage including a first mounting surface;

at least one first antenna array configured to image a breast of the patient, the at least one first antenna array removably mounted to the at least one carriage, the at least one first antenna array including:

a housing having a second mounting surface, wherein the second mounting surface of each antenna array engages the first mounting surface of the at least one carriage when the corresponding antenna array is mounted thereto, and at least one antenna coil located within the housing; and at least one second antenna array removably mounted to the base plate, wherein the antenna support structure is further configured to be moved independently from the first patient support structure and the second patient support structure and wherein the antenna support structure is configured to be positioned between the first patient support structure and the second patient support structure on the scan table during the medical imaging.

10. The antenna support structure of claim 9 wherein the base plate is generally planar and includes a lower surface and an upper surface, wherein the lower surface is positionable on the scan table and the upper surface has the at least one rail mounted to it.

11. The antenna support structure of claim 10 wherein:

the at least one rail includes a first rail and a second rail;

each of the first rail and the second rail are mounted to the upper surface of the base plate and spaced apart from each other; and the at least one carriage is movably mounted between the first rail and the second rail.

12. The antenna support structure of claim 11 further comprising:

a junction box mounted to the base plate outside of the first and second rails, wherein one of the first rail and the second rail includes a slot extending longitudinally along the rail and wherein the at least one carriage includes an electrical cable connected between the at least one carriage and the junction box and the electrical cable is routed through the slot in the rail.

13. The antenna support structure of claim 12 wherein:

the at least one second antenna array includes a first electrical connector, the junction box includes a second electrical connector, and the first electrical connector and the second electrical connector are connected when the at least one second antenna array is mounted to the base plate.

14. The antenna support structure of claim 9 further comprising:

a first electrical connector mounted, at least in part, within the housing of the first antenna array, wherein an opening extends through the second mounting surface and the first electrical connector is accessible via the opening in the second mounting surface; and a second electrical connector mounted at least in part within the at least one carriage, wherein the first mounting surface includes an opening through which the second electrical connector is accessible, wherein the first and second electrical connectors are operatively connected when the first antenna array is mounted to the at least one carriage.

15. The antenna support structure of claim 14 wherein the first mounting surface includes at least one additional opening, the antenna support structure further comprising a spring-biased ejector protruding through the at least one additional opening, wherein:

when the housing of the first antenna array is removed from the at least one carriage, the spring-biased ejector is in an unbiased state and the spring-biased ejector protrudes through the additional opening;

when the housing of the first antenna array is mounted to the at least one carriage, the spring-biased ejector is in a biased state and the spring-biased ejector is compressed generally even to the first mounting surface; and the spring-biased ejector disconnects the first and second electrical connectors, separating the first antenna array from the carriage when the carriage is moved to a home position, wherein the home position is a position along the at least one rail where the first antenna array is loaded on or removed from the carriage.

* * * * *